US006528642B1

(12) United States Patent
Duval et al.

(10) Patent No.: US 6,528,642 B1
(45) Date of Patent: Mar. 4, 2003

(54) MONO-AND DI-DERIVATIVES OF CYCLODEXTRINS, SYNTHESIS THEREOF AND PURIFICATION AND USE THEREOF IN SUPPORT

(75) Inventors: Raphaël Duval, Notre Dame de Gravenchon (FR); Hubert Lévêque, Lillebonne (FR)

(73) Assignees: Institut Francais du Petrole (FR); Chiralsep S.A.R.L. (FR)

( * ) Notice: Subject to any disclaimer, the term of this patent is extended or adjusted under 35 U.S.C. 154(b) by 0 days.

(21) Appl. No.: 09/382,578

(22) Filed: Aug. 25, 1999

Related U.S. Application Data

(62) Division of application No. 09/131,241, filed on Aug. 7, 1998, now Pat. No. 6,042,723.

(30) Foreign Application Priority Data

Aug. 29, 1997 (FR) ............................................ 97 10817

(51) Int. Cl.⁷ ............................................ C08B 37/16
(52) U.S. Cl. ...................................... 536/103; 536/124
(58) Field of Search ........................... 514/58; 536/103, 536/124; 528/25; 525/474; 210/198.2, 635, 656

(56) References Cited

U.S. PATENT DOCUMENTS

| | | | | | |
|---|---|---|---|---|---|
| 5,198,429 | A | * | 3/1993 | König et al. ................... | 514/58 |
| 5,268,442 | A | * | 12/1993 | Bradshaw et al. ............ | 528/25 |
| 5,391,592 | A | * | 2/1995 | Herbrechtsmeier et al. . | 523/107 |
| 5,403,898 | A | * | 4/1995 | Bradshaw et al. .......... | 525/474 |
| 5,959,089 | A | * | 9/1999 | Hannessian ................. | 536/18.7 |
| 6,042,723 | A | * | 3/2000 | Duval et al. ............. | 210/198.2 |

FOREIGN PATENT DOCUMENTS

| | | | |
|---|---|---|---|
| EP | 608 703 A1 | * | 8/1994 |
| EP | 899 272 A1 | * | 3/1999 |
| EP | 985 681 A1 | * | 3/2000 |
| EP | 985 682 A1 | * | 3/2000 |
| JP | 07-053 605 A2 | * | 2/1995 |
| WO | WO 98/22795 A1 | * | 5/1998 |

OTHER PUBLICATIONS

Breslow et al., "Sequence Selective Binding of Peptides by Artificial Receptors in Aqueous Solution," *Journal of the American Chemical Society*, 120(14), 3536–3537 (Apr. 15, 1998; web published Mar. 28, 1998).*

Forgo et al., "Synthesis and Properties of Modified Cyclodextrins," *10th International Cyclodextrin Symposium*, Abstract 1–o7, University of Michigan, Ann Arbor, MI, May 21–24, 2000.*

König et al. (II), "Gas Chromatographic Enantiomeric Separation of Agrochemicals Using Modified Cyclodextrins," *Journal High Resolution Chromatography*, 14(8), 530–536 (1991).*

Venema et al., "The Enantioselectivity of Modified Cyclodextrins: Studies on Interaction Mechanisms," *Journal of High Resolution Chromatography*, 14(10), 676–680 (Oct., 1991).*

Ling et al., "Research on PbS Nanoparticles Coated with 2,6–O–Diallyl–beta–CD," *Chinese Chemical Letters*, 8(3), 263–266 (1997).*

Baer et al., "Synthesis of a Cycloheptaose Consisting of (1–>4)–Linked 7–Amino–6,7–dideoxy–a–D–gluco– hetopyranosyl Units: A New Analog of Cyclomaltoheptaose," *Carbohydrate Research*, 235, 129–135 (Nov. 4, 1992).*

Takeo et al., "Derivatives of a–Cyclodextrin and the Synthesis of 6–O–a–D–glucopyranose–a–cyclodextrin," *Journal of Carbohydrate Chemistry*, 7(2), 293–308 (May, 1988).*

Lai et al., "Piezoelectric Quartz Crystal Detection of Benzene Vapour Using Chemically Modified Cyclodextrins", *Journal of the Chemical Society, Perkin Transactions II*, (Issue No. 3), 319–324 (Mar., 1988).*

Menger et al., "Synthesis and Properties of a Surfactant–Cyclodextrin Conjugate," *Tetrahedron Letters*, 27(23), 2579–2582 (1986).*

Bergeron et al. (I), "The Role of Strain Energy in Cycloamylose Substrate Complexation," *Bioorganic Chemistry*, 5(2), 197–202 (Jun., 1976).*

Bergeron et al. (II), "Selective Alkylation of Cycloheptaamylose," *Bioorganic Chemistry*, 5(1), 121–126 (1976).*

Collins et al., *Monosaccharides Their Chemistry and Their Roles in Natural Products*, John Wiley & Sons, New York, NY, 1995, only pp. 344–347 supplied.*

Hanessian et al., "The Synthesis of Functionalized Cyclodextrins As Scaffolds and Templates for Molecular Diversity, Catalysis, and Inclusion Phenomena," *Journal of Organic Chemistry*, 60(15), 4786–4797 (Jul. 28, 1995).*

Schürig et al., "Gas Chromatographic Enantiomer Separation on Polysiloxane–Anchored Permethyl–β–Cyclodextrin (Chirasil–Dex)," *Jouranl of High Resolution Chromatography*, 13, 713–717 (Oct., 1990).*

* cited by examiner

*Primary Examiner*—Johann Richter
*Assistant Examiner*—L E Crane
(74) *Attorney, Agent, or Firm*—Millen, White, Zelano & Branigan, P.C.

(57) ABSTRACT

Mono- and di-derivatives of cyclodextrins are completely defined, also a method for their synthesis and purification, functionalised cyclodextrins obtained from these derivatives, and the synthesis of supports comprising these cyclodextrin derivatives. Use of the supports for the preparation or separation of enantiomers, for asymmetric synthesis, for catalysis, for the preparation or separation of geometrical isomers or positional isomers, or for the preparation or separation of organic molecules with a hydrophobic nature is also described.

6 Claims, 3 Drawing Sheets

Figure 1:
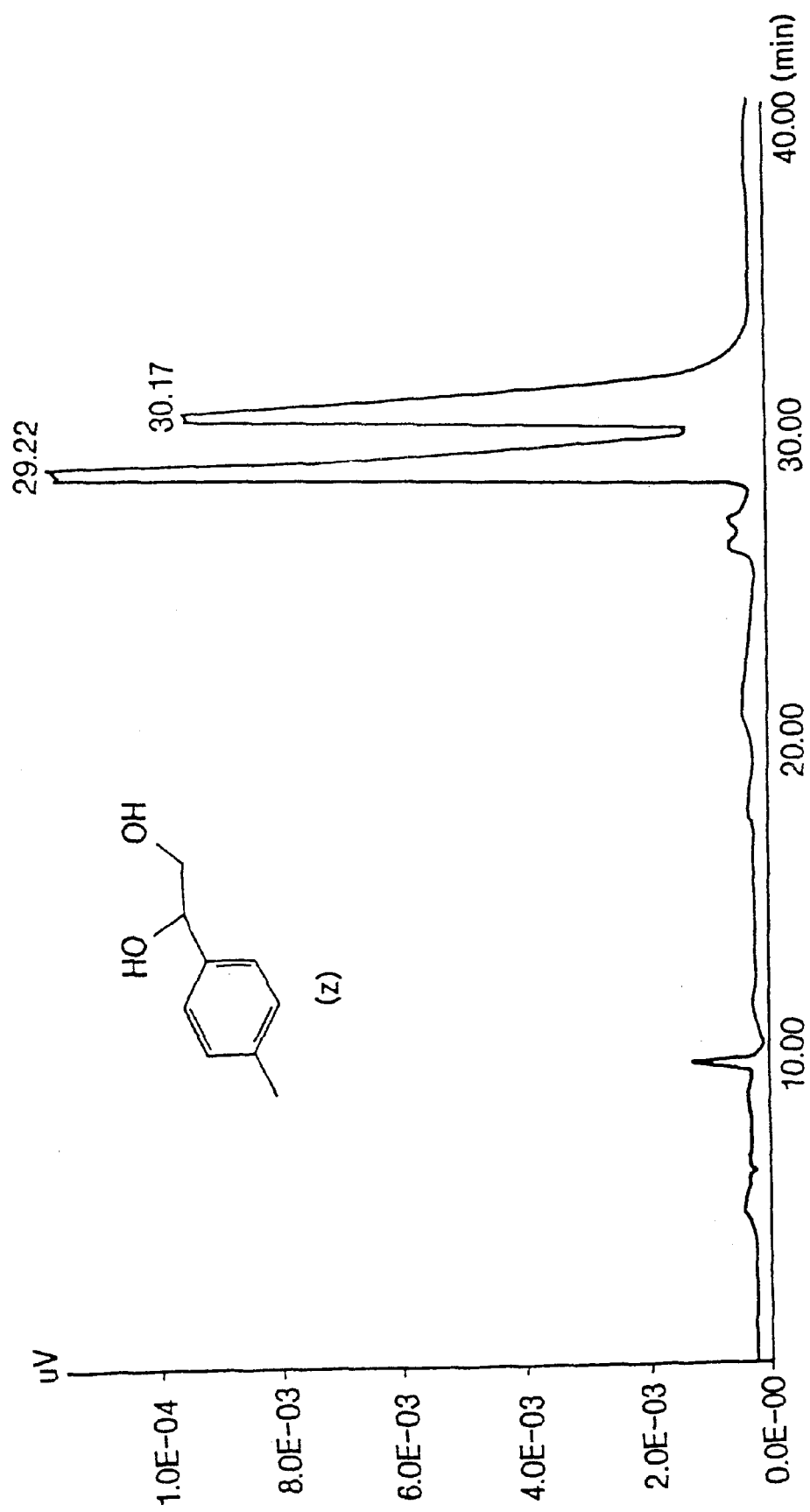

MONO-AND DI-DERIVATIVES OF CYCLODEXTRINS, SYNTHESIS THEREOF AND PURIFICATION AND USE THEREOF IN SUPPORT

This is a divisional, of Ser. No. 09/131,241 filed Aug. 7, 1998 now U.S. Pat. No. 6,042,723.

The invention relates to a method comprising synthesis and purification of mono- and di-derivatives of cyclodextrins (abbreviated to CD), also the synthesis of supports from these cyclodextrin derivatives. These novel supports comprise one or two spacer arms regioselectively bonded to the 2, 3 or 6 position of a glucoside unit of the cyclodextrin.

The invention also relates to the use of these supports for the preparation or separation of enantiomers, for asymmetric synthesis, for catalysis, for the preparation or separation of geometrical isomers or positional isomers or for the preparation or separation of organic molecules with a hydrophobic nature.

The invention also relates to a method comprising synthesis of polymers obtained from mono- and di-derivatives of cyclodextrins, also to the synthesis of supports from these cyclodextrin polymers.

The invention also relates to the use of the supports for the preparation or separation of enantiomers, for asymmetric synthesis, for catalysis, for the preparation or separation of geometrical isomers, or for the preparation or separation of organic molecules with a hydrophobic nature.

Separating organic molecules using the encapsulation properties of cyclodextrins has been carried out for a large number of years. See in particular M. L. Bender: "Cyclodextrin Chemistry"—Springer Verlag—New York, 1978; R. J. Clarke: "Advanced Carbohydrates Chemistry and Biochemistry", 1988, 46, 205; W. Saenger: ANGEW CHEM.—Int. Edit., 1980, 19, 344; G. Wenz: ANGEW CHEM.—Int. Edit., 1996, 33, 803. These properties are currently widely exploited on an industrial scale in the perfume and flavouring industries and in the pharmaceutical industry. See in particular J. Szejtli: MED. CHEM. REV. 1994, 14, 353, and D. Duchene: J. COORD. CHEM., 1992, 21, 223.

The use of cyclodextrins bonded to supports has demonstrated their ability to separate and prepare organic molecules and positional isomers (see in particular Y. Kawaguchi: ANAL. CHEM. 1983, 55, 1852–1857, and K. Fujimura: ANAL. CHEM. 1983, 55, 446–450) or geometrical isomers (E/Z isomerism)—(see in particular Y. Inoue: J. AM. CHEM. SOC. 1995, 117, 11033–11034).

More recently, the same supports have been used to separate or prepare enantiomers (see in particular K. Takahaschi: J. INCL. PHENOM., 1994, 17, 1) or a variety of molecules by catalysis (see in particular G. Wenz: ANGEW. CHEM.—Int. Edit., 1996, 33, 803). This field has been expanding for about twenty years, both on the analytical and on a preparative level. This is particularly true in the pharmaceutical industry, where the health authorities of industrialised countries require the separate study of optical isomers of any chiral compound used in a medicament composition.

Native or derivative cyclodextrins have been the subject of a number of studies and cyclodextrins, bonded or otherwise to supports, are commercially available.

Supports based on cyclodextrin derivatives or based on polymers from these derivatives have not been chemically defined and are in the form of mixtures of mono- and poly-derivatives. Cyclodextrins contain a large number of hydroxyl functions of almost equivalent reactivity and up until now, chemically and regioselectively defined CD derivatives produced on an industrial scale have not existed.

The present invention provides access to mono- and di-derivatives of pure and regioselectively defined cyclodextrins as regards the position of the derivative on the glucoside unit: the 2, 3 or 6 position.

The derivatives can be grafted onto a mineral or organic matrix via a covalent hydrocarbon bond carrying a thioether function. The ensemble constitutes a support with increased selectivity over known supports for the following applications:

separation or preparation of organic molecules with a hydrophobic nature;

separation or preparation of positional isomers or geometrical isomers;

separation or preparation of enantiomers; or asymmetric synthesis of chiral molecules.

The increased selectivity of these supports is an important factor for enabling them to be used on a laboratory, pilot or industrial scale, as it can reduce production costs.

The supports of the invention, which are completely original, can produce chromatographic performances which are hitherto unknown, in particular in the field of separation of enantiomers by liquid chromatography: the selectivities obtained prove to be higher than those currently obtained with commercially available cyclodextrin-based chiral columns.

A number of parameters combine to produce this unexpected result:

The regioselectivity of the bond between the glucoside unit of the cyclodextrin and the spacer arm connecting it to the organic or mineral support. The synthesis technique and purification of the cyclodextrin mono-derivative can produce practically pure derivatives bonded in the 2, 3 or 6 position of the glucoside unit of the cyclodextrin.

Synthesis of a support using a single spacer arm between the very high purity cyclodextrin mono-derivative and the functionalised silica gel.

The presence of a supplemental interaction side constituted by the thioether, sulphoxide or sulphone function on the spacer arm, enabling the creation of Van Der Waals type bonds with the solute, with the latter being engaged in other reactions with the cyclodextrin.

The combination of these interactions leads to the supports of the invention, which have a higher discriminating power over those described in the prior art.

The state of the art is represented by European patent application EP-A-0 608 703 and United States patent U.S. Pat. No. 4,539,399, which describes chromatographic supports based on cyclodextrins. Those supports are not chemically defined as their method of synthesis leads to undifferentiated mixtures of compounds mono- and poly-substituted in the three positions (2, 3 and 6) of the glucoside unit. Chromatographic supports using a spacer arm containing a thioether function have been widely used to separate enantiomers. As an example, Rosini et al. described the immobilisation of cinchona bark alkaloids with that type of arm in TETRAHEDRON LETT. 26, 3361–3364, 1985. More recently, Tambute et al. described the immobilisation of tyrosine derivatives using the same technique in NEW J. CHEM. 13, 625–637, 1989. More recently still, Caude et al. disclosed the results of their studies and have demonstrated the advantage of the thioether arm in terms of chemical stability in J. CHROMATOGR. 550, 357–382, 1991.

Salvadori et al. have shown the efficacy of quinine derivatives in the form of osmium tetraoxide adducts for the oxidation of asymmetric olefins in homogeneous and heterogeneous phases, in CHIRALITY 4, 43–49, 1992. Such derivatives were present in the form of copolymers of acrylonitrile and quinine derivatives carrying a sulphoxide spacer arm. The efficacy of the presence of the sulphoxide function was not discussed in that type of support used for asymmetrical synthesis.

Further, a route to mono-alkenylcyclodextrins has been described by Hanssian et al. in J. ORG. CHEM. 1995, 60, 4786–4797. They described the synthesis of mono-2-allyl-α-cyclodextrin by the action of allyl bromide and lithium hydride in the presence of dimethylsulphoxide. The reaction medium was then purified with acetone, then chromatographic purification was carried out on virgin silica gel in a 90/10 v/v, then in a 40/10 v/v, acetonitrile/water mixture to obtain a monoallyl-α-cyclodextrin. However, the authors admit, the data obtained from proton nuclear magnetic resonance showed the presence of 20% of mono-6-allyl-α-cyclodextrin.

Schürig et al (J. HIGH RESOLUT. CHROMATOGR. 13, 713–717, 1990) have described the synthesis of allyl, pentenyl and octenyl derivatives of β-CD which were then grafted onto hydrogenopolysiloxanes (methylhydrogenopolysiloxane+dimethylpolysiloxane=copolymer) by hydrosilylation in toluene in the presence of dihydrogenoplatinum hexachloride. No structural study on the chemical purity and regioselectivity of the CD derivatives could confirm the 6 position as the attachment point for the alkenyl moieties. This 6 regioselectivity has been contested by Ciucanu and Konig in J. CHROMATOGR. A, 685, 166–171, 1994. These latter also described the synthesis and purification of permethyl- and perpropylmono-O-pent-1-enyl-β-cyclodextrin, then hydrosilylation of the double bond with dimethoxymethylhydrosilane or dichloromethylhydrosilane.

Yi et al. (J. CHROM. A, 673, 219–230, 1994) described the synthesis of 4-allyloxy benzoyl type mono-derivatives in the 2 or 3 position, the remainder of the hydroxyl groups having been permethylated. However, the field of the nuclear magnetic resonance apparatus used for such compounds (200 MHz) appears to have been a little weak for complete identification of the products obtained, because of the complexity of the problem to be solved and the precision required for integrating the ethylene signals. Those derivatives were grafted onto hydromethylpolysiloxanes (copolymer of octamethylcyclotetrasiloxane and dimethoxyditolylsilane).

K. Fujita describes, in J. Am. CHEM. SOC., 108, 2030–2034, 1986, the synthesis and purification of mono- and 3A–3C and 3A–3D-di-O-(β-naphthalene-sulphonyl)-β-cyclodextrin.

Yi et al. described, in J. HETEROCYCLIC CHEM. 32, 621, 1995, different routes to type 6A–6C and 6A–6D-di-O-(4-alkoxyphenyl) di-derivatives which are completely permethylated. The regioselectivity of the compounds obtained was controlled by using ditosylates of differing sizes. The compounds were copolymerised with a dihydrodioctyldecamethylhexasiloxane.

Bradshaw et al. described the synthesis of di-derivatives of type 6A–6B-di-O-(4-allyloxyphenyl) per-O-methyl-β-cyclodextrin type cyclodextrins using 2,4-dimethoxy-1,5-benzenedisulphonyldichloride. The derivatives were then copolymerised with a dihydrogenododecamethylhexasiloxane. See in particular ANAL. CHEM. 67, 23, 4437–4439, 1995.

Thuaud et al. described the synthesis of polymers containing cyclodextrin units by condensing the latter with bifunctional reactants (epichlorhydrin) (J. CHROMATOGR. 555, 53–64, 1991 and CHROMATOGRAPHIA, 36, 373–380, 1993). The structure of the polymer was not regioselectively defined.

That polymer has previously been synthesised by P. Sugiura et al. (BULL. CHEM. SOC. JPN. 62, 1643–1651, 1989) who had also used diepoxides as polymerising agents.

Polymerisation of ethylenic monomers has been carried out for a great many years ("Principles of Polymer Chemistry", Paul J. Flory, Editor, Cornell Press New York, 1953 edition). Homopolymerisation of mono-derivatives and di-derivatives of cyclodextrin containing a polymerisable carbon—carbon double bond has not been described before the present invention. It is carried out using a free radical initiator (an azo or peroxide type compound) at a temperature of 50° C. to 200° C., the preferred temperature range being 100° C. to 150° C. The reaction periods are from 1 to 48 hours. Preferred solvents are toluene, dioxane, chloroform, tetrahydrofuran, alcohols, dimethylformamide, dimethylsulphoxide or a mixture of these solvents.

The polymerisation reaction may or may not be carried out in the presence of a support, the latter preferably being surface modified with ethylenic functions, hydrogenosilanes or thiols.

Copolymerisation of ethylenic monomers has also been widely described, for example in "Principles of Polymer Chemistry" cited above. The synthesis conditions are identical to those used for homopolymerisation (described above). The comonomers used can be monofunctional (for example styrene), bifunctional (for example divinylbenzene, ethanediol or tetramethyldisiloxane) or polyfunction (for example glycerol trimethacrylate).

The copolymerisation reaction may or may not be carried out in the presence of a support, the latter preferably being surface modified by ethylene, hydrogenosilane or thiol functions. Polymerisation by hydrosilylation is known per se and described in J. CHROMATOGR., 594, 283–290, 1992. The basic technique described in that article can be used to prepare cyclodextrin polymers. The reaction is preferably carried out in the presence of a catalyst, generally a metal complex, for example a platinum or rhodium complex, at temperatures of 50° C. to 180° C., preferably about 100° C. Solvents which are inert to the polymerisation reaction taking place are used to dilute the reaction medium. Preferred solvents are toluene, dioxane, chloroform, tetrahydrofuran and xylene or mixtures of these solvents.

The reaction times are 1 to 48 hours as the kinetics of the hydrolysilylation polymerisation reaction are relatively slow.

The polymerisation reaction may or may not be carried out in the presence of a support, the latter preferably being surface modified by styryl, methacryloyl, methacrylamido, acrylamido, hydrogenosilane, vinyl or thiol functions.

Cyclodextrins are cyclic oligosaccharides with general formula:

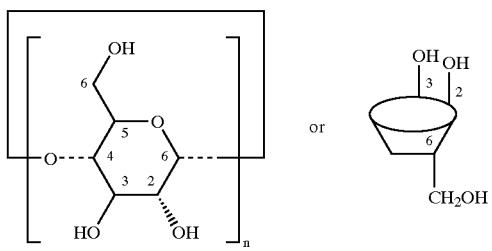

The value n=6 corresponds to an α-cyclodextrin; the value n=7 corresponds to a β-cyclodextrin; the value n=8 corresponds to a γ-cyclodextrin.

The alcohol functions can readily be transformed by a variety of groups such as acid chlorides and isocyanates, to produce esters or carbamates. Reaction with halides produces ethers. Whatever the reaction conditions used in the reactions, they always result in mixtures. Usually, a number of osidic units are concerned in the reactions described above with a regioselectivity (2, 3 or 6 position on the osidic unit) which is difficult to control.

The present invention describes a method for synthesis and purification of pure mono- and di-derivatives of cyclodextrin regioselectively bonded in the 2, 3 or 6 position of an osidic unit. Cyclodextrin di-derivatives may concern two different osidic units. The following general terminology is thus used:

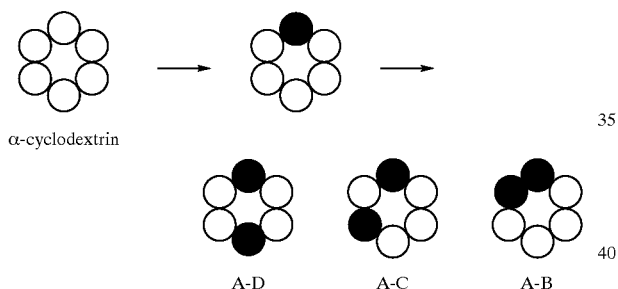

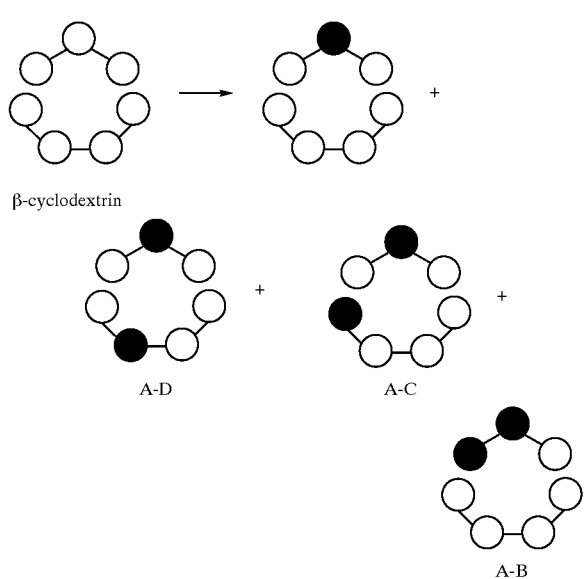

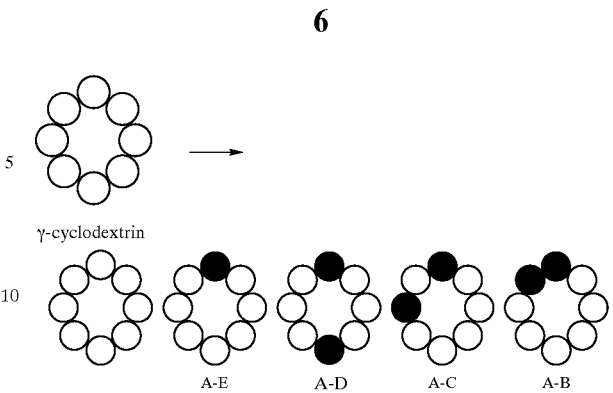

Pure cyclodextrins with formulae (Xa), (Xb), (Xc), (XIa), (XIb), (XIc), (XId), (XIe) and (XIf) can be obtained using the following reaction scheme:

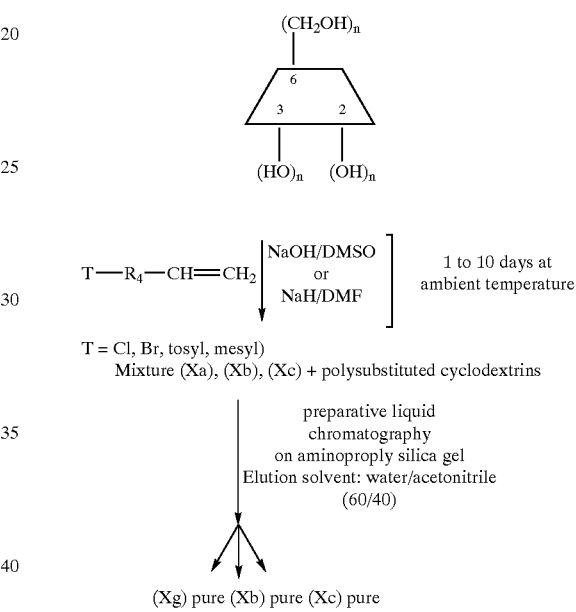

and pure (XIa), (XIb), (XIc), (XId), (XIe) and (XIf).

The reaction between cyclodextrin and the compound with general formula T—$R_4$—CH=$CH_2$ can be carried out in solvents usually used in organic chemistry, such as water, dioxane, tetrahydrofuran, toluene, halogenated solvents (chloroform, methylene chloride . . . ), ketones (acetone, methylethylketone), acetonitrile, dimethylformamide, dimethylsulphoxide or mixtures of these solvents.

For reasons of solubility of the starting product and the products formed, preferred solvents are dimethylsulphoxide and dimethylformamide. The low reactivity of the primary and secondary hydroxyl groups of cyclodextrins necessitates the use of large excesses of T—$R_4$—CH=$CH_2$. The reaction temperature is 0° C. to 100° C., preferably between 0° C. to 30° C., to encourage the formation of mono- and di-derivatives and prevent the formation of polyderivatives. Reaction times are 1 to 10 days. After reaction, the reaction medium is generally poured onto acetone to precipitate the different constituents of the reaction medium and isolate them by filtering.

The precipitate is purified by preparative chromatography on a silica or alumina gel, or zirconia or titanium oxide, or on an organic polymer type support, such as styrene-divinylbenzene or polyvinyl alcohol.

These supports are surface modified by amino functions (for example aminopropyl), alkyl functions (for example octyl or octadecyl), aryl functions (for example phenyl), or diol functions.

The chromatographic procedure is carried out using water-soluble organic solvents such as acetonitrile, ethanol, methanol, isopropanol, dioxane, dimethylsulphoxide and dimethylformamide, mixed with water, at temperatures of 0° C. to 80° C., preferably 15° C. to 30° C.

Separation is monitored by refractive index detection and the purity of the cyclodextrin derivatives is determined by HPLC or TLC.

HPLC is carried out on a 100 Å, 5 μm aminopropyl silica column with dimensions of 250×4.6 mm, RI detection, eluting with acetonitrile/water, 70/30 by volume. The TLC system uses virgin "Merck" silica plates. The mobile phase is a 50/50 by volume mixture of 30% ammonia and ethanol. Iodine vapour is used to reveal.

The purified products are isolated by vacuum evaporating the water and organic solvent at a temperature of 40° C. to 80° C. bulk in a vacuum varying from 1 to 50 mm of mercury.

The chemical balance of the reaction is as follows:

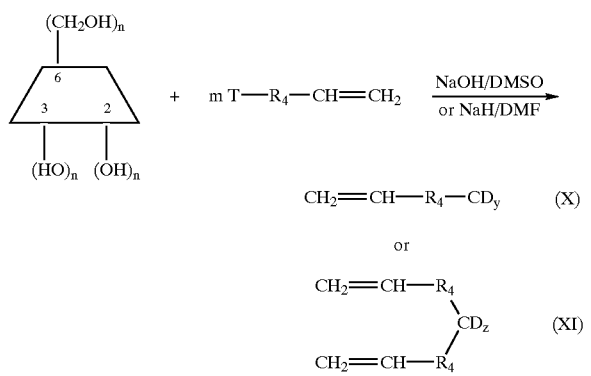

where m is 1 to 24 (moles/mole of CD).

Formula (X) represents the possible mono-O-alkenyl-CD formulae: namely mono-2-O-, mono-3-O- and mono-6-O-.

Formula (XI) represents the alkenyl-CD di-derivatives, the derivatives being formed on the same glucoside unit or on different units (positions A-B, A-C, etc . . . ) with identical or different regioselectivities.

Compounds with general formulae (X) and (XI) can be grafted onto functionalised supports to produce supports with general formulae (Iy), (Ia), (Ib), (Iz), (Ic) and (Id), the vacant hydroxyl functions also may or may not be derived before or after grafting to the support. As an example, 3-mercaptopropyltrimethoxysilane was grafted to a silica gel via a covalent bond as follows:

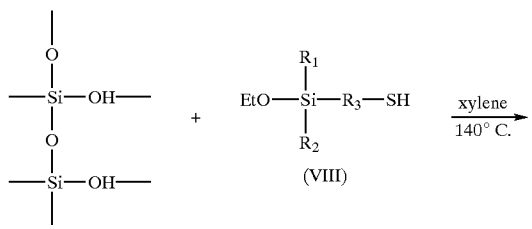

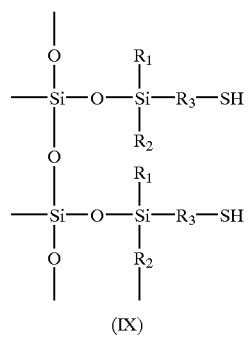

where $R_1 = R_2 = CH_3$—$CH_2$—O— and $R_3 = $—$(CH_2)_3$—

The reaction was carried out in xylene to eliminate firstly the water contained in the silica gel and then to eliminate the ethanol formed by hydrolysis of the ethoxysilane functions. The support obtained had the following characteristics:

%C=5.26

%S=2.68

%H=1.10 giving, on calculation, a thiol function density of 0.85 mmol/g, or 0.89 if it is considered that 2 or 3 ethoxysilanes have effectively reacted with the silica gel. 30% of the "theoretical" SiOH had been modified. Starting from a density of $8 \times 10^{-6}$ moles of $SiOH/m^2$ with a support of 360 $m^2/g$, we arrive at a density of 28 mmoles/g of silica. The support obtained, "mercaptopropylsilica" or "thiol" silica, was then reacted with a compound with formula (X) or (XI). Anti-Markovnikov addition of the double bond to the silica thiol was carried out in the presence of a free radical initiator (C. Rosini, TETRAHEDRON LETT. 1985, 26 (28), 3361, and A. Tambute, NEW J. CHEM., 1989, 13, 625–637).

As an example, mono-2-O-pentenyl-β-cyclodextrin was grafted to the thiol support as shown in the following reaction scheme:

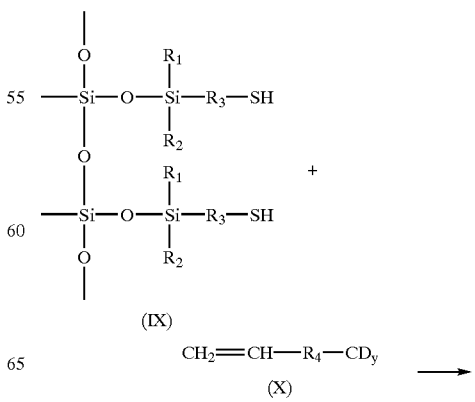

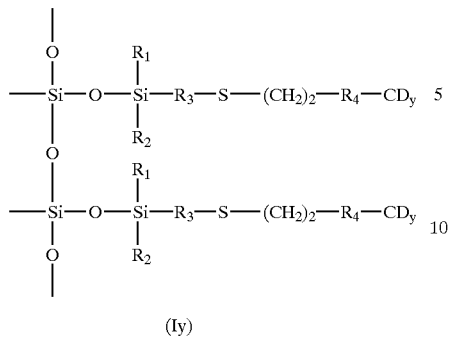

(Iy)

where $R_1=R_2=CH_3-CH_2-O-$ $R_3=-(CH_2)_3-$
$R_4=-(CH_2)_3-$

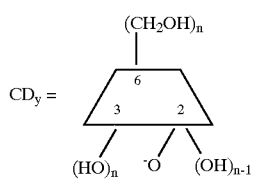

and n=7.

The reaction was carried out in chloroform under reflux in the presence of azo-isobutyronitrile (AIBN). The supports obtained form part of the invention.

These supports could then be oxidised to transform the thioether function to a sulphoxide using hydrogen peroxide ("Organic compounds of bivalent sulphur" vol. 2, pp. 64–66, Chemical Publishing Company, New York, 1960), indobenzene dichloride (Barbieri, J. CHEM. SOC. C659, 1968), sodium metaperiodate (Leonard, J. ORG. CHEM., 27, 282, 1962) or tertiobutyl oxychloride (Walling, J. ORG. CHEM. 32 1286, 1967) or peracids.

The sulphoxide supports obtained could be oxidised to sulphones using potassium permanganate or hydrogen peroxide (Heubert, CHEM. COMM., 1036, 1968 and Curci, TETRAHEDRON LETT., 1749, 1963).

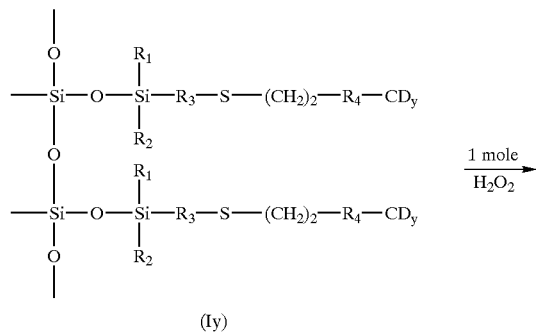

(Iy)

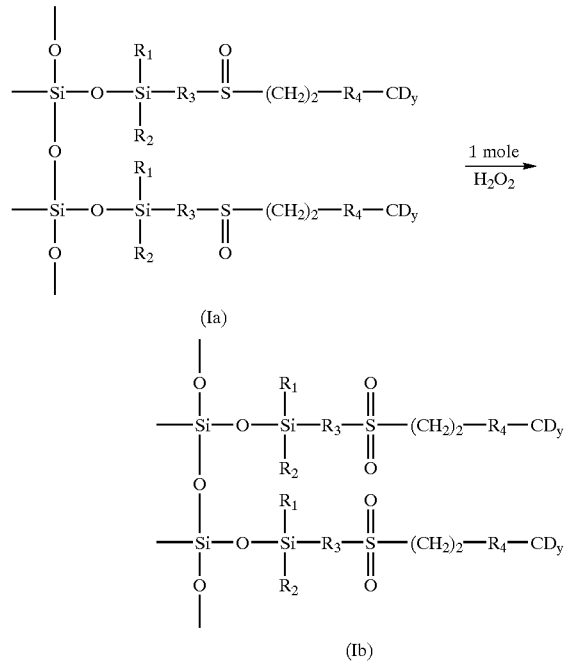

(Ib)

The preferred oxidising agent is hydrogen peroxide. The reaction solvent is generally water or an alcohol or an organic solvent which is miscible with water. The bulk temperature is 10° C. to 40° C. The reaction time is 1 to 8 hours.

As an example, the above support, a mono-2-O-pentyl-β-cyclodextrin grafted onto thiol silica, was directly oxidised to the sulphone with excess hydrogen peroxide in solution in water/methanol at 25° C. The reaction kinetics were monitored by following the hydrogen peroxide content in the reaction medium by quantitative analysis using a reducing agent.

The oxidised support, of type (Ib), had the following structure:

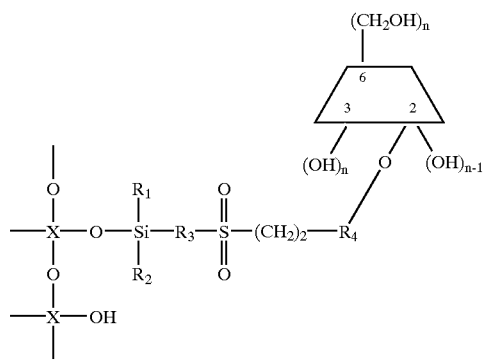

where n=7
$R_3=R_4=-(CH_2)_3-$
$R_1=R_2=CH_3-CH_2-O-$
or OH
or O-support

The performances of supports (Iy) and (Ib) were compared by separating enantiomers using high performance liquid chromatography (HPLC). The supports were compressed under 500 bars pressure in 250 mm×4.6 mm HPLC tubes (length by internal diameter) under identical conditions.

$k'_1$ and $k'_2$ are partition ratios, i.e., when I=1 or 2, $k'_1=(t_{R1}-t_0)/t_0$, where $t_{R1}$ is the retention time of compound I and $t_0$ is the dead time;

α is the relative retention ratio: $\alpha=(t_{R2}-t_0)/(t_{R1}-t_0)=k'_2/k'_2$;

$R_S$ is the peak resolution:

$$R_s = \frac{1}{4}\left(\frac{\alpha-1}{\alpha}\right)\left(\frac{k'_2}{1+k'_2}\right)(N)^{1/2},$$

where N is the number of plates;

$N=a(t_R/\omega)^2$ where ω=the peak width at a given ordinate, proportional to the square of the standard deviation or variance $\sigma^2$ by the relationship $\omega^2=a\sigma^2$; giving $N=16(t_R/\omega)^2=5.54(t_R/\omega)^2$.

The results are shown in Table 1 on the next page.

This support had the following structure:

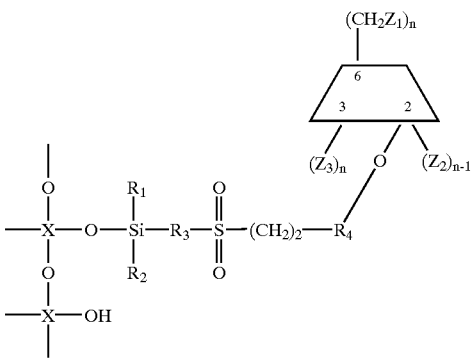

TABLE I

| COMPOUND | MOBILE PHASE | SPACER ARM | FLOW RATE | CAPACITY FACTORS | SELECTIVITY |
|---|---|---|---|---|---|
| Dansyl-leucine | Triethylammonium acetate/ 1% pH = 5 acetonitrile 60/40 | Thioether | 1 ml/min | K'1 = 21.08 K'2 = 29.00 | α = 1.37 |
| Dansyl-leucine | Triethylammonium acetate/ 1% pH = 5 acetonitrile 60/40 | Sulphone | 1 ml/min | K'1 = 2.12 K'2 = 4.21 | α = 1.98 |
| Dansyl-threonine | Triethylammonium acetate/ 1% pH = 5 methanol 60/40 | Thioether | 1 ml/min | K'1 = 9.25 K'2 = 10.67 | α = 1.15 |
| Dansyl-threonine | Triethylammonium acetate/ 1% pH = 5 methanol 60/40 | Sulphone | 1 ml/min | K'1 = 1.08 K'2 = 1.29 | α = 1.19 |
| Benzaithione | Triethylainmonitiin acetate/ 1% pH = 5 acetonitrile 60/40 | Thieoether | 1 ml/min | K'1 = 10.42 K'2 = 11.42 | α = 1.096 |
| Benzaithione | Triethylammonium acetate/ 1% pH = 5 acetonitriile 60/40 | Sulphone | 1 ml/min | K'1 = 2.37 K'2 = 2.79 | α = 1.17 |
| Ethylphenyl-hydantoin | Triethylammonium acetate/ 1% pH = 5 methanol 80/20 | Thioether | 1 ml/min | K'1 = 13.25 K'2 = 14.08 | α = 1.043 |
| Ethylphenyl hycdantoin | Triethylamnionium acetate/ 1% pH = 5 methanol 80/20 | Sulphone | 1 ml/min | K'1 = 8.56 K'2 = 9.42 | α = 1.10 |

There is an interest in modifying all or some of the hydroxyl functions of a cyclodextrin to modify the encapsulation properties thereof. Complete modification of the hydroxyl functions confers different properties on the cyclodextrin to those of native cyclodextrins. As an example, methylated cyclodextrins are more soluble than those obtained from native CDs.

The support for the preceding example was modified by the action of an isocyanate. Adding alcohols to isocynates is known per se (Satchell, CHEM. SOC. REV. 4, 231–250, 1975). The reaction is generally carried out in a basic medium (for example pyridine, triethylamine) in the presence of an organometallic catalyst (Davies, J. CHEM. SOC. C2663, 1967).

The bulk temperature is from 50° C. to 150° C. It is preferably kept between 80° C. and 120° C. bulk. The reaction period is between 1 and 48 hours and is adjusted as a function of the reactivity of the isocyanate used towards the alcohol to be transformed.

In the preceding support example, the primary and secondary alcohol functions, vacant in the β-CD, were percarbamated.by 3,5-dimethylphenylisocyanate in a 50/50 triethylamine/pyridine mixture at 80° C. bulk over 24 hours in, the presence of dibutylin laurate.

where n=7
$R_3=R_4=$—$(CH_2)_3$—
$R_1=R_2=CH_3$—$CH_2$—O—
or OH
or O-support
and $Z_1=Z_2=Z_3=$

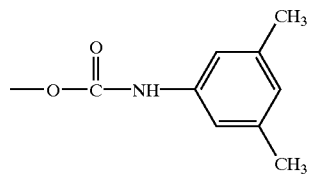

Figure 2:
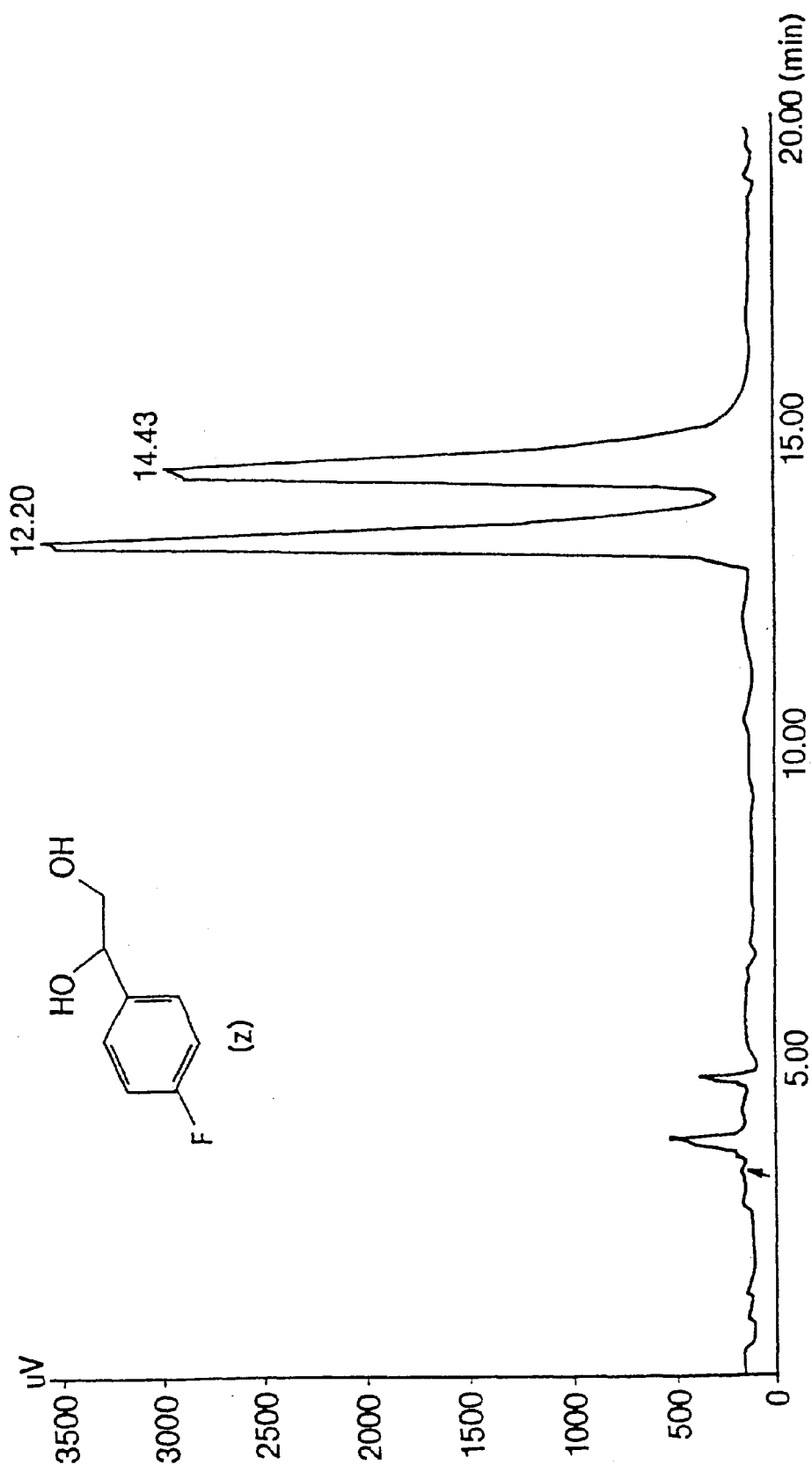
Figure 3:
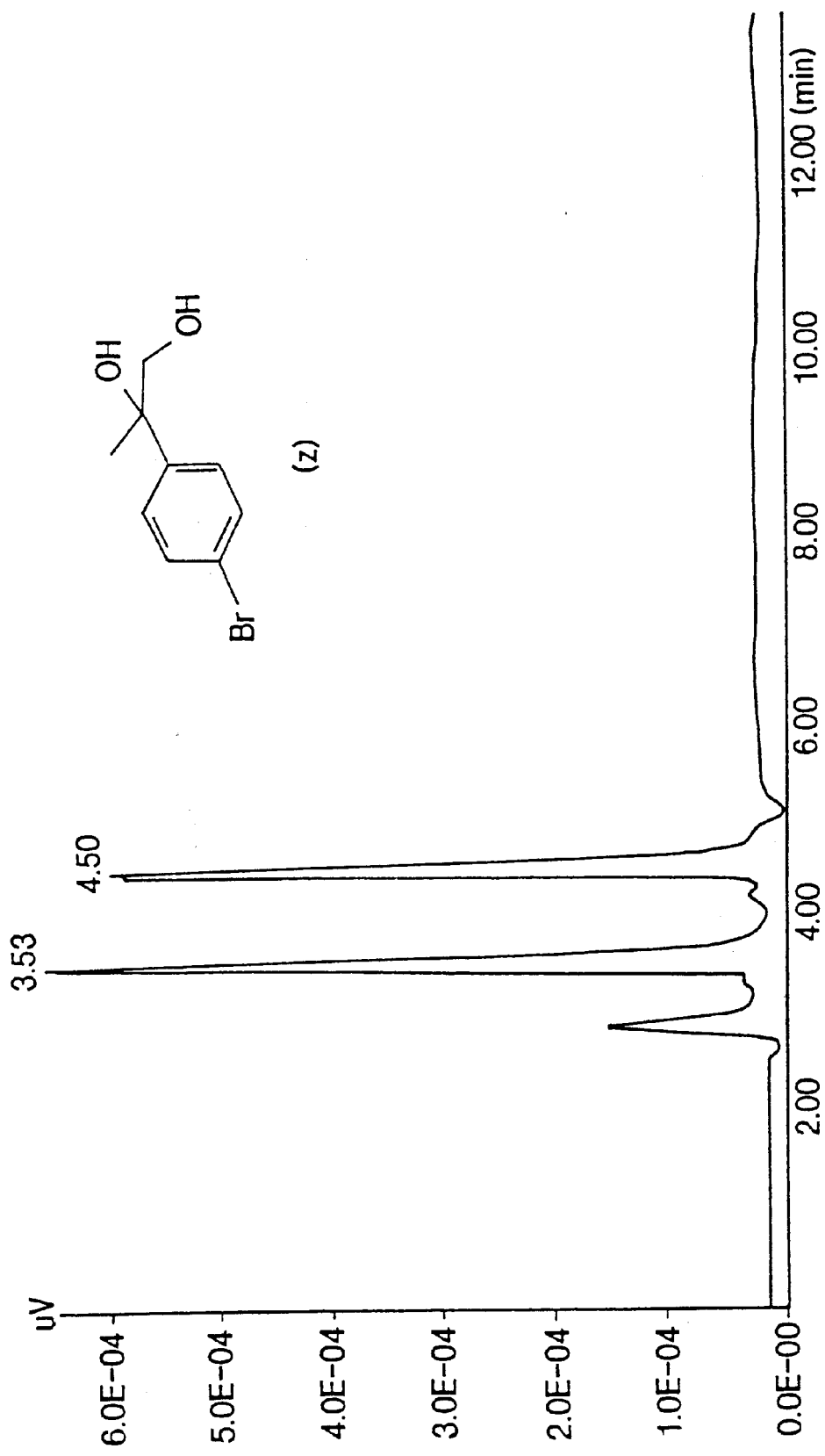

This support was used as a chromatographic support for separating enantiomers. The results are shown in FIGS. 1–3 wherein

FIG. 1 shows:

HPLC SEPARATION OF (+/−)-1-(4-TOLYL)-ETHANEDIOL

Column dimensions: 250×4.6 mm with 50×4.6 pre-column

Quantity of solute: 10 μg in 10 μl

Flow rate: 1 ml/min

Detection: UV 254 nm

Mobile phase: heptane/chlorobutane/methanol 75/17.5/7.5

K'1=8.07
K'2=8.65
Relative retention ratio α=1.07
FIG. 2 shows:
HPLC SEPARATION OF (+/−)-1-(4-FLUOROPHENYL)-ETHANEDIOL
   Column dimensions: 250×4.6 mm with 50×4.6 pre-column
   Quantity of solute: 10 μg in 10 μl
   Flow rate: 1 ml/min
   Detection: TV 254 nm
   Mobile phase: heptane/methyl tertiobutyl ether/methanol 60/36/4
   K'1=3.16
   K'2=3.51
   Relative retention ratio α=1.11
FIG. 3 shows:
HPLC SEPARATION OF (+/−)-1-(4-BROMOPHENYL)-2-HYDROXYPROPANOL
   Column dimensions: 250×4.6 mm with 50×4.6 pre-column
   Quantity of solute: 10 μg in 10 μl
   Flow rate: 1 ml/min
   Detection: UV 254 nm
   Mobile phase: methyl tertiobutyl ether/methanol 90/10
   K'1=0.28
   K'2=0.64
   Relative retention ratio α=2.32

Cyclodextrin polymers currently form the subject matter of a variety of research aimed at producing products which can exploit the encapsulation properties for cyclodextrins on an industrial scale in absorption/desorption processes of compounds to be recovered (flavour concentrates produced in aqueous media by a microbiological route, for example) or eliminated (elimination of bitterness from beer malt). In this, the routes to the production of and exploitation of mono- and di-derivatives of perfectly defined cyclodextrins developed in this invention enable the synthesis of CD homo- and copolymers from characterised monomers.

As an example, 2A-2D-di-2-O-allyl-β-cyclodextrin was copolymerised in the presence of ethanedithiol to obtain a straight chain polymer. Condensation of dithiol compounds with diolefins is generally carried out in the presence of free radicals (Marvel, J. AM. CHEM. SOC., 70, 993, 1948 and Mayo, CHEM. REV., 27, 387, 1940). The reaction was carried out between 50° C. and 200° C. in the presence of an organic solvent with a suitable boiling point.

The chemical reaction was as follows:

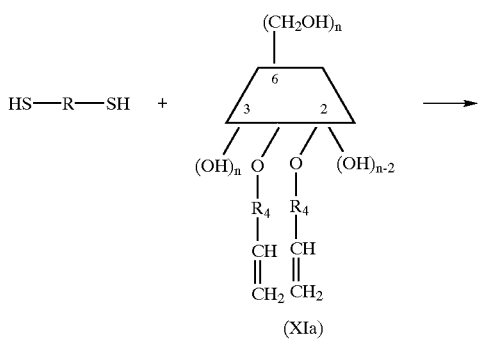

(XIa)

-continued $$(-S-R-S-CH_2CH_2-R'-CH_2CH_2-)_{n1}$$

where R=—(CH$_2$)$_2$—
   R$_4$=—CH$_2$—
   n=7
   1<n1<100000
and

R' = 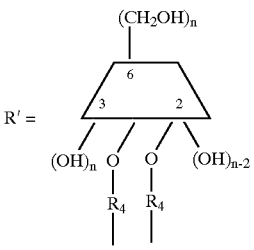

The 2A-2D-di-2-O-allyl-β-cyclodextrin (type (XIa) compound) was copolymerised in chloroform under reflux, in the presence of AIBN for 20 days, in the presence of a slight excess of ethanedithiol. The excess ethanedithiol was eliminated by distillation and the polymer obtained re-dissolved in chloroform. Silica which had been surface modified with hydrogenosilane functions (H. W. Stourman, CHROMATOGRAPHIA, 25, 4, 265–271, 1988) was brought into contact with the polymer and the ensemble was heated to chloroform reflux in the presence of AIBN for 5 days. The reaction product was filtered and dried for 24 hours at 50° C. under vacuum.

The compound obtained was termed "POLY-THIOOETHYL-2,2-DIALLYL-β-CD" or "PTE-2,2-AL-β-CD".

An HPLC column was filled with this support. A number of tests were carried out.

SEPARATION OF ORTHO, META- AND PARA-NITROPHENOLS AND OTHER STRUCTURAL ISOMERS 3 g of PTE-2,2-AL-β-CD was suspended in ethanol (20 ml). The suspension was poured into an HPLC filling system (R. Rosset, M. Caude and A. Jardy in "Chromatographies en phases liquide et supercritiquet" ["Liquid and Supercritical Phase Chromatography"] 1991 edition, pages 177 to 183, (ed. Masson).

The filling pressure was fixed at 600 bar and the column used had the following dimensions: 250 mm length and 4.6 mm internal diameter. The column was used in a chromatographic system with UV detection at 254 nm. 10 ug quantities were injected. Different eluting systems were tested: the values of k' were as follows: (dead time $t_o$ was determined using methanol)

| Nitrophenol isomers | Water/ methanol 60/40 | Water/ acetonitrile 60/40 | Water/ methanol 50/50 | Water acetonitrile 50/50 |
|---|---|---|---|---|
| META | 5.2 | 4.7 | 5.2 | 4.3 |
| ORTHO | 20.4 | 7.6 | 15.4 | 5.1 |
| PARA | 43.2 | 13.1 | 36.4 | 8.9 |

-continued

| Cresol isomers | Water/methanol 50/50 |
| --- | --- |
| META | 5.2 |
| ORTHO | 15.4 |
| PARA | 24.6 |

| Nitrotoluene isomers | Water/methanol 80/20 |
| --- | --- |
| META | 5.9 |
| ORTHO | 7.6 |
| PARA | 11.1 |

| Toluidine isomers | Water/methanol 80/20 |
| --- | --- |
| META | 5.5 |
| ORTHO | 8.8 |
| PARA | 11.0 |

| Aminophenol isomers | Water/methanol 80/20 |
| --- | --- |
| META | 5.4 |
| ORTHO | 7.7 |
| PARA | 9.8 |

PURIFICATION OF CYCLODEXTRIN-GLUCOSYLTRANSFERASE (CG-TASE) FROM BACILLUS CIRCULANS E 192 BY AFFINITY CHROMATOGRAPHY

The enzymatic activity of CG-Tase was determined by measuring the cyclisation potential using the VIKMON phenolphthalein method ("Proceedings of the First International Symposium on Cyclodextrin", J. Szejtli, D. Revdel, Publishing Co., London, 1982, page 69). A Unit "U" was the quantity of enzyme which produces 1 μmole of β-CD per minute under standard conditions of temperature (50° C.) and pH (7.0) in the presence of 5% (weight/volume) of maltodextrins (Glucidex 12® sold by Roquette Frères, Lestrem, France) as a substrate.

The PTE-2,2-AL-β-CD HPLC column was equilibrated for 24 hours with the following eluent:

10 mM tris-HCl buffered at pH 7.5;
20 mM $CaCl_2$
0.02% (weight/volume) of $NaN_3$ The percolation rate was 1 ml/min and the pressure was 850 bars.

5 mg of CG-Tase dissolved in 2 ml of water was injected onto the column and then rinsed with the above tris-HCl eluent. Protein elution was shown by UV detection at 280 nm. Purified CG-Tase was eluted in the following mixture:

10 mM of tris-HCl buffer to pH 7.5
10 mM $CaCl_2$
0.02% (weight/volume) of $NaN_3$
1% (weight/volume of β-cyclodextrin The purified CG-Tase was eluted after 150 ml and the core fraction was concentrated by ultrafiltration (Y 10 AMICON membrane) then lyophilised.

The specific activity of the purified CG-Tase was 125 U/mg, i.e., a gain of 500% on the initial activity (25 U/mg).

A further copolymerisation technique can be carried out using a dihydrogenosilxane. This reaction was commented on above.

2A-2D-di-O-2-allyl-β-cyclodextrin (type XIa) compound) was copolymerised with 1,1,3,3-tetramethyldihydrogenosiloxane in toluene at 60° C. over 24 hours. A slight excess of 1,1,3,3-tetramethyldihydrogenosiloxane was used. This excess was distilled off at the end of the reaction.

The reaction was as follows:

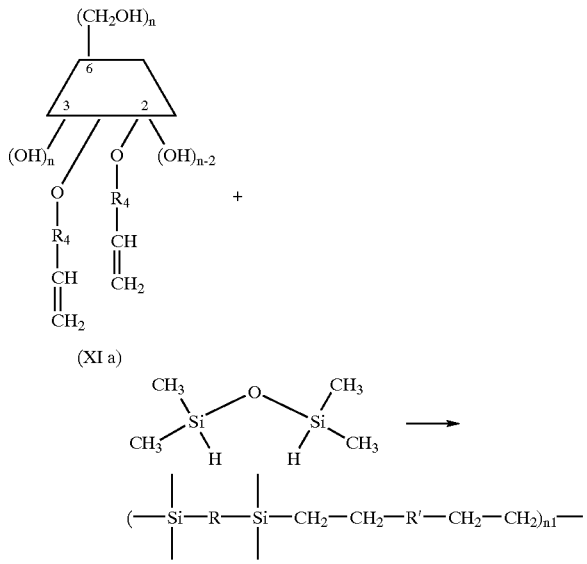

where R=oxygen
$R_4$=—$CH_2$—
n=7
$1 < n_1 < 100,000$ and R' =

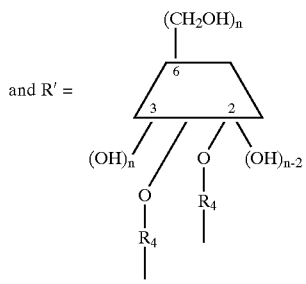

A support surface modified with sulphydryl functions (with general formula (X)), for example "thiol" or "mercaptopropyl" silica, was brought into contact with the polymer dissolved in chloroform in the presence of AIBN. It was refluxed for 48 hours. The support was filtered, washed then dried.

The compound obtained-was termed "POLYSILOX-2,2 DIALLYL-β-CD". It is used as a chromatographic support and produced under the conditions described above.

SEPARATION OF DANSYLATED AMINO ACIDS

The test chromatographic conditions and solutes were those described by Willie L. Hinze in ANALYTICAL CHEMISTRY, vol. 57, No. 1, January 1985, pages 237 to 242.

The relative retention ratios a obtained for each dansylated amino acid (1-N,N-[((dimethylaminonaphthalene)-5-sulphonamide))] type derivative) was unexpectedly always higher than that obtained by Hinze.

| | | |
|---|---|---|
| α-amino-N-butyric acid | α = | 1.29 |
| arginine | | 1.32 |
| methionine | | 1.17 |
| norleucine | | 1.32 |
| norvaline | | 1.17 |
| phenylalanine | | 1.28 |
| serine | | 1.23 |
| tryptophan | | 1.01 |
| threonine | | 1.32 |
| valine | | 1.22 |

SEPARATION OF STRUCTURAL IOSMERS

The HPLC chromatographic conditions by D. W. Armstrong in ANALYTICAL CHEMISTRY 1983, 55, 2375–2377 were reproduced.

| | | |
|---|---|---|
| ortho-aminobenzoic acid | K' = 4.0 | |
| meta-aminobenzoic acid | K' = 7.8 | α(meta/ortho) = 1.95 |
| para-aminobenzoic acid | K' = 10.1 | α(para/ortho) = 2.52 |

The relative retention ratios obtained by Armstrong were respectively 1.54 (m/o) and 1.82 (p/o).

The chromatographic supports of the invention have chemical structures with formulae (Iy), (Ia), (Ib), (Iz), (Ic) and (Id):

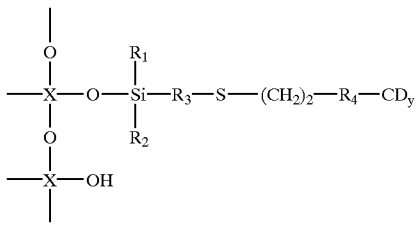

(Iy)

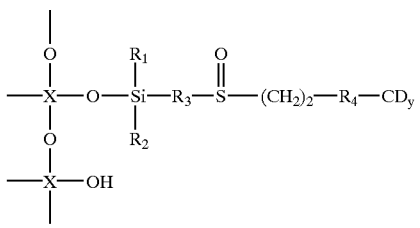

(Ia)

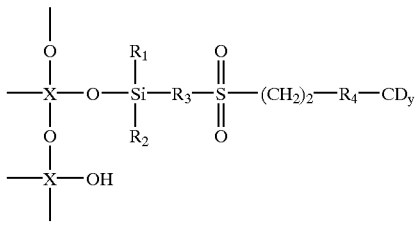

(Ib)

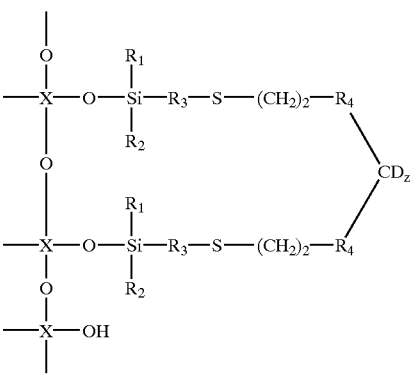

(Iz)

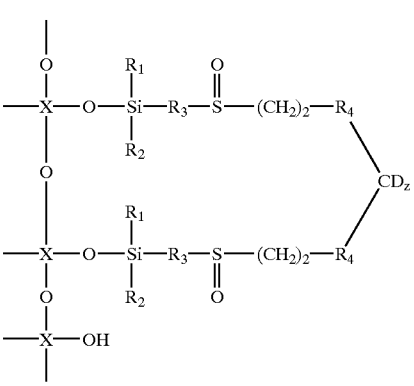

(Ic)

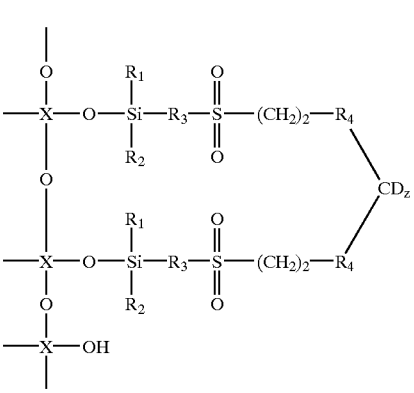

(Id)

where:

X represents Si, Zr, Ti, Mg, or Al or an organic polymer, $R_1$ and $R_2$, which may be identical or different, represent a halogen atom or a linear or branched $C_1$ to $C_6$ alkyl, or a linear or branched $C_1$ to $C_6$ alkoxy group, a hydroxyl group, an aryl group, optionally substituted by one or more identical or different halogen atoms or alkyl, alkoxy, hydroxyl or trihalogenoalkyl groups; $R_3$ and $R_4$, which may be identical or different, represent a $C_1$ to $C_{20}$ alkyl group, or an aryl group, possibly substituted by a $C_1$ to $C_{20}$ alkyl group;

$CD_y$ represents:

a native cyclodextrin with formula (IIy), (IIIy) or (IVy):

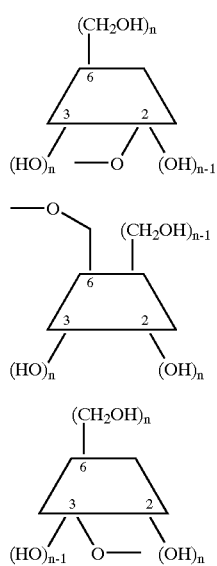

where n=6→α-cyclodextrin; n=7→β-cyclodextrin; or n=8→γ-cyclodextrin;
or a modified cyclodextrin with formula (Vy), (VIy) or (VIIy):

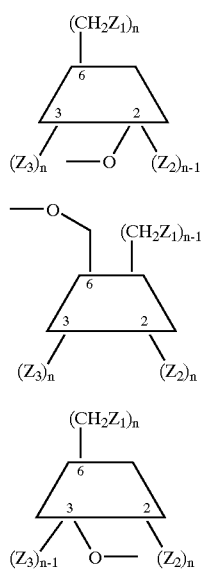

where:
n has the same meaning as that given for formulae (IIy), (IIIy) and (Ivy);
$Z_1$ represents $-Y_1W_1$
$Z_2$ represents $-Y_2W_2$
$Z_3$ represents $-Y_3W_3$ and
$Y_1$, $Y_2$ and $Y_3$ which may be identical or different, represent an oxygen atom, a sulphur atom, an amino group, or a sulphoxide or sulphone group;
$W_1$, $W_2$ and $W_3$, which may be identical or different, represent:
a group $A_2-A_1-A_0$ where:
$A_0$ represents $-CO-$ or $-CS-$;
$A_1$ represents a bond or an amino group;
$A_2$ represents a linear or branched alkyl group ($C_1-C_{24}$), optionally substituted by an aryl group or an aryl group itself optionally substituted by a linear or branched ($C_1-C_{24}$) alkyl group, given that the aryl groups can also be substituted by one or more identical or different halogen atoms(s), or linear or branched ($C_1-C_6$) alkyl group(s), hydroxyl groups, or linear or branched ($C_1-C_6$) trihalogenoalkyl groups;
a linear or branched ($C_1-C_{24}$) alkyl group, in particular methyl, ethyl or hydroxypropyl;
a ($C_3-C_8$) cycloalkyl group;
a heterocyclic group;
or an osidic or polysidic group, in particular glucosyl, diglycosyl, thioglycosyl or maltosyl.

$Z_1$, $Z_2$ or $Z_3$ represents an aldehyde function, a carboxylic acid or ester function, a sulphinamide or sulphimide function, a hydroxyl function, a sulphonic acid function, a sodium, potassium or ammonium sulphate function, an ethyl-, propyl- or butylsulphonic function, a phosphoric acid function or a sodium, lithium, potassium or ammonium phosphate function;

$Z_1$ and $Z_3$ can represent a 3,6-anhydro function.

$Z_1$ and $Z_3$ can represent a 2,3-anhydro function. $CD_z$ represents:
a native cyclodextrin with formula ($II_z$); ($III_z$); ($IV_z$); ($II_{zz}$); ($III_{zz}$) or ($IV_{zz}$):

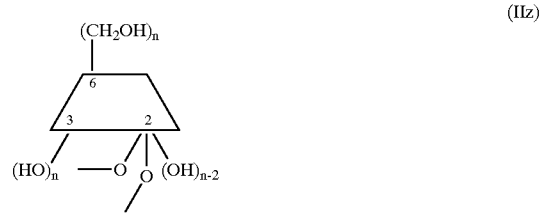

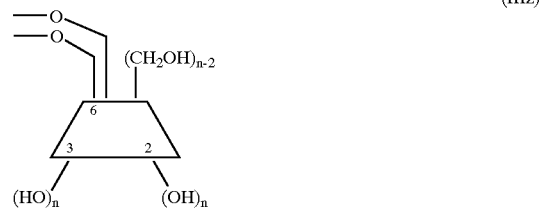

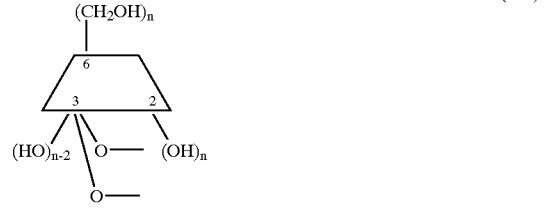

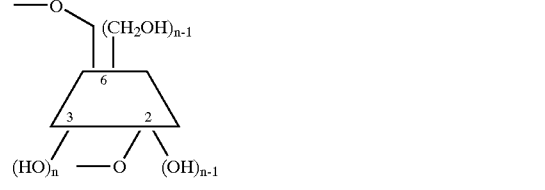

-continued

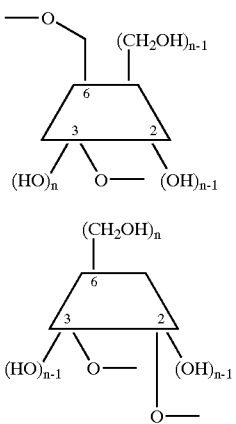

where n=6→α-cyclodextrin; n=7→β-cyclodextrin; or n=8→γ-cyclodextrin; or a modified cyclodextrin with formula $(V_z)$, $(VI_z)$, $(VII_z)$, $(V_{zz})$, $(VI_{zz})$ or $(VII_{zz})$:

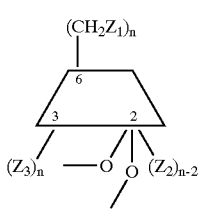
(Vz)

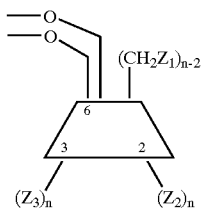
(VIz)

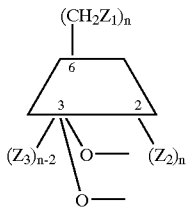
(VIIz)

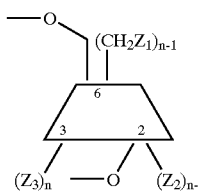
(Vzz)

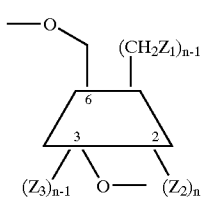
(VIzz)

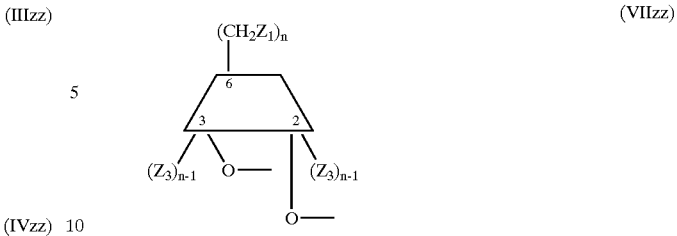

where:
n has the meaning given for formulae $(II_z)$, $(III_z)$, $(IV_z)$, $(II_{zz})$; $(III_{zz})$ or $(IV_{zz})$;
$Z_1$ represents —$Y_1W_1$
$Z_2$ represents —$Y_2W_2$
$Z_3$ represents —$Y_3W_3$ and
$Y_1$, $Y_2$ and $Y_3$ which may be identical or different, represent an oxygen atom, a sulphur atom, an amino group, or a sulphoxide or sulphone group;
$W_1$, $W_2$ and $W_3$, which may be identical or different, represent:
a group $A_2$—$A_1$—$A_0$ where:
$A_0$ represents —CO— or —CS—;
$A_1$ represents a bond or an amino group;
$A_2$ represents a linear or branched alkyl group $(C_1$–$C_{24})$, optionally substituted by an aryl group or an aryl group itself optionally substituted by a linear or branched $(C_1$–$C_{24})$ alkyl group, given that the aryl groups can also be substituted by one or more identical or different halogen atom(s), or linear or branched $(C_1$–$C_6)$ alkyl group(s), hydroxyl groups, or linear or branched $(C_1$–$C_6)$ trihalogenoalkyl groups;
a linear or branched $(C_1$–$C_{24})$ alkyl group, in particular methyl, ethyl or hydroxypropyl;
a $(C_3$–$C_6)$ cycloalkyl group;
a heterocyclic group;
or an osidic or polyosidic group, in particular glucosyl, diglycosyl, thioglycosyl or maltosyl.
$Z_1$, $Z_2$ or $Z_3$ represents an aldehyde function, a carboxylic acid or ester function, a sulphinamide or sulphimide function, a hydroxyl function, a sulphonic acid function, a sodium, potassium or ammonium sulphate function, an ethyl-, propyl- or butylsulphonic function, a phosphoric acid function or a sodium, lithium, potassium or ammonium phosphate function;
$Z_1$ and $Z_3$ can represent a 3,6-anhydro function.
$Z_2$ and $Z_3$ can represent a 2,3-anhydro function.
In the above definitions, the aryl groups are preferably phenyl groups, optionally substituted.

The very high purity of the supports of the invention renders them particularly useful for separating enantiomers from racemic mixtures.

The invention also pertains to a process for producing chromatographic supports with formulae (Iy), (Ia), (Ib), (Iz), (Ic) and (Id).

This process is characterised in that in a first step, a silica gel carrying mercaptoalkyl groups is synthesised which in a second step is grafted onto a pure cyclodextrin substituted with an ethylenic chain.

The sulphoxide and sulphone functions are then obtained by treatment with known chemical oxidising agents to create these types of functions from the thioether group and which are, for example, selected from the following: iodobenzene chloride, sodium metaperiodate, tertio-butyl-oxychloride, peracids, hydrogen peroxide and potassium permanganate.

Using purified cyclodextrin derivatives enables supports to be obtained which have a perfectly defined chemical structure.
The synthesis is illustrated by the following scheme:
Step 1
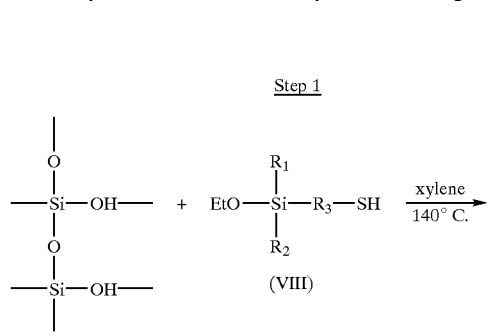
(VIII)
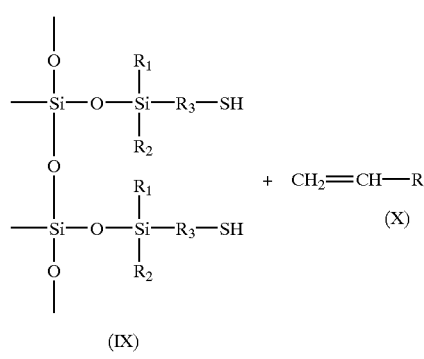
(IX)
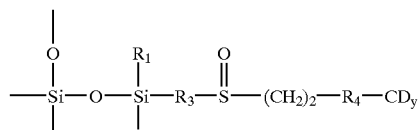
(Ia)
↓ oxidising agent
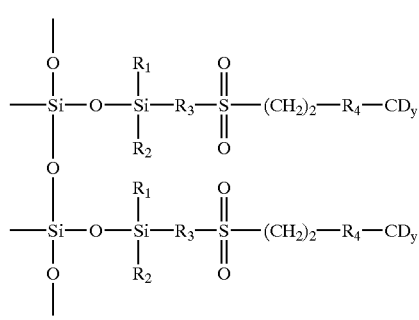
(Ib)
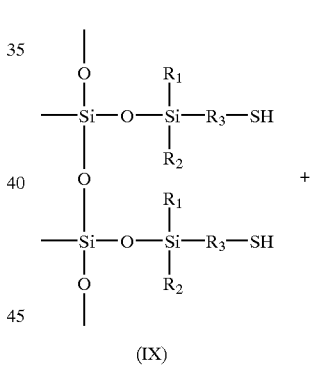
(IX)
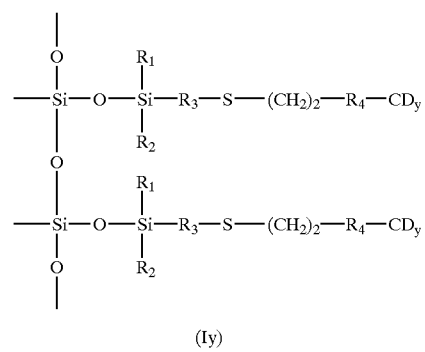
(Iy)
↓ oxidising agent
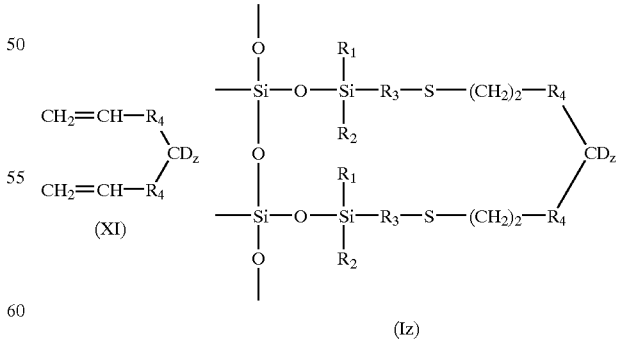
(Iz)
↓ oxidising agent

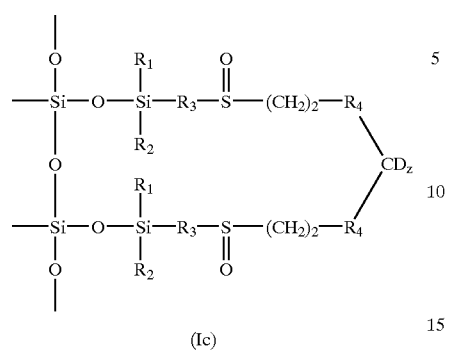

(Ic)

↓ oxidising agent

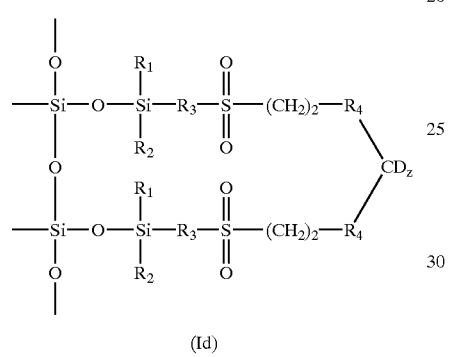

(Id)

↓ oxidising agent

In compounds with formulae (X) and (XI), R has the same meaning, as in formulae (Iy), (Ia), (Ib), (Iz), (Ic), (Id). $CD_y$ has the same meaning as in formulae (Iy), (Ia) or (Ib), i.e., it represents any of formula $(II_y)$; $(III_y)$, $(IV_y)$ for native cyclodextrins, $(V_y)$, $(VI_y)$, $(VII_y)$ for modified cyclodextrins.

$CD_z$ has the same meaning as in formulae (Iz), (Ic) or (Id), i.e., represents any one of formula $(II_z)$, $(III_z)$, $(IV_z)$ and $(II_{zz})$, $(III_{zz})$, $(IV_{zz})$ for native cyclodextrins, $(V_z)$, $(VI_z)$, $(VII_z)$ and $(V_{zz})$, $(VI_{zz})$, $(VII_{zz})$ for modified cyclodextrins.

The compounds with formula (X) can be represented by the following formulae (Xa) to (Xf).

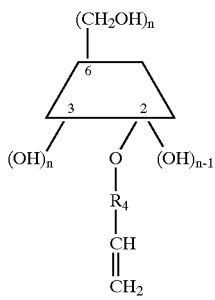

(Xa)

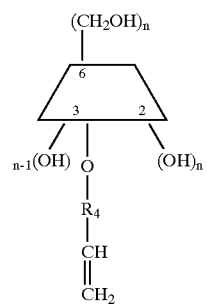

(Xb)

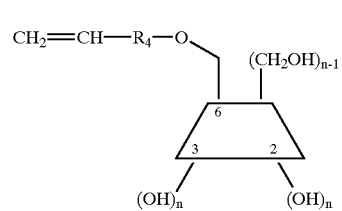

(Xc)

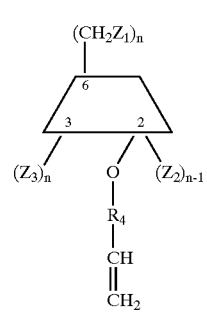

(Xd)

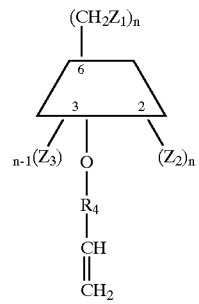

(Xe)

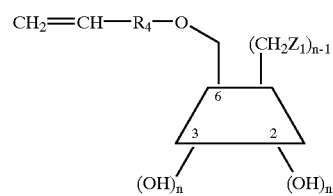

(Xf)

where n=6→α-cyclodextrin; n=7→β-cyclodextrin; or n=8→γ-cyclodextrin.

The compounds with formula (XI) can be represented by the following formulae (XIa) to (XIl).

(XIa)
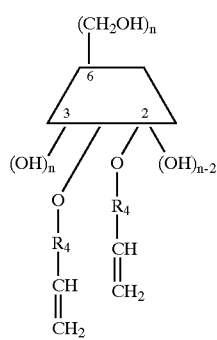
(XIb)
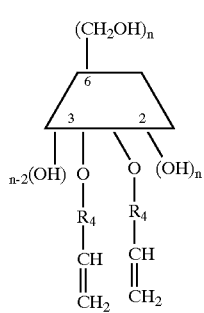
(XIc)
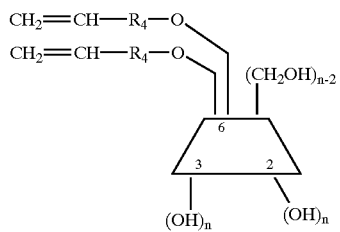
(XId)
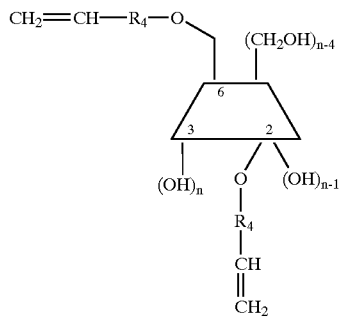
(XIe)
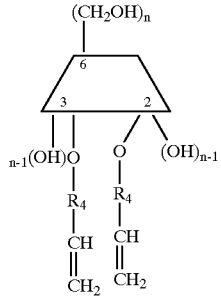
(XIf)
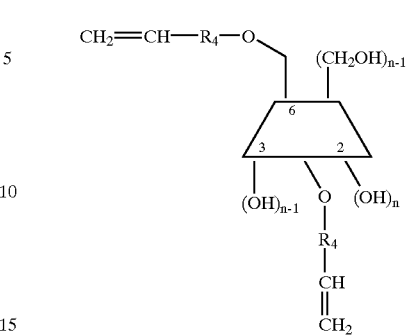
(XIg)
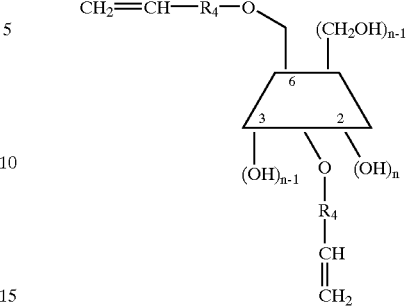
(XIh)
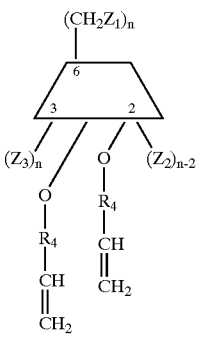
(XIi)
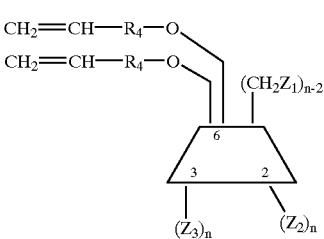
(XIj)
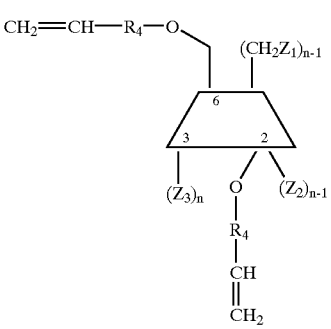

-continued

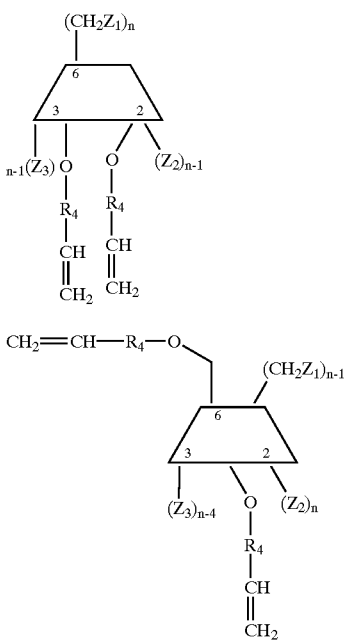

where n=6→α-cyclodextrin; n=7→β-Cyclodextrin; or n=8→γ-cyclodextrin.

The invention also concerns polymers obtained from monomeric compounds with formulae (Xa) to (Xf) and (XIa) to (XII) with general formulae:

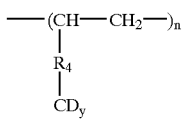
(XII)

obtained by homopolymerisation of

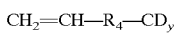
(X)

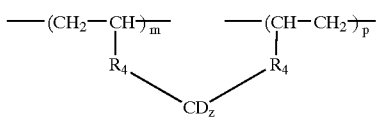
(XIII)

obtained by homopolymerisation of

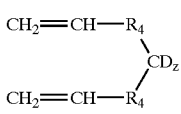
(XI)

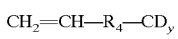
(XIV)

obtained by copolymerisation of $CH_2{=}CH{-}R_4{-}CD_y$ (X)

and

(XI)

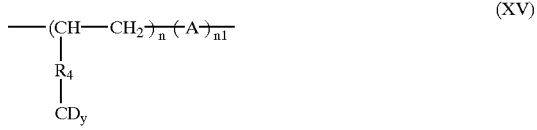
(XV)

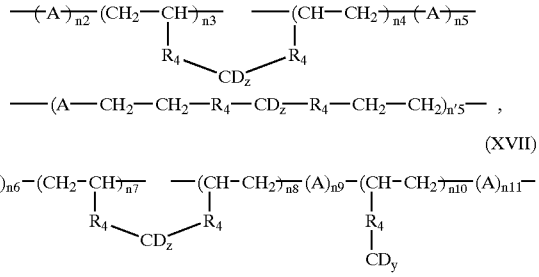
(XVI)

$-(A-CH_2-CH_2-R_4-CD_z-R_4-CH_2-CH_2)_{n'5}-$, (XVII)

with n, $n_1$, $n_2$, $n_3$, $n_4$, $n_5$, $n'_5$, $n_6$, $n_7$, $n_8$, $n_9$, $n_{10}$, $n_{11}$, m and p, in the range 1 to 100000 with A of type

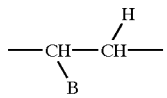

and where B represents an aryl or polyaryl group containing 5 to 30 carbon atoms, optionally substituted by heteroatoms, or an alkyl group containing 2 to 30 carbon atoms, optionally substituted by heteroatoms or a halogen atom;

or with A of type —X—L—X— where X represents a sulphur atom (thioether function) or a sulphoxide function or a sulphone function;

L represents $(CH_2)_n$ or an alkyl group, an alkyl substituted by alcohol or acid functions, or an aryl group optionally substituted by a heteroatom;

or with A of type

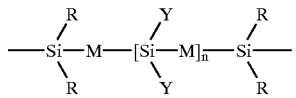

where R represents an alkyl or aryl group containing 1 to 4 carbon atoms, or hydrogen or a mixture of the two;

M represents $(CH_2)_m$ or oxygen, with m from 0 to 10;

y represents $-O-Si(R)_3$, $-O-Si(R)_2H$ or the group R; and n is 0 to 3000.

The invention also concerns polymers obtained from monomers (Xa) to (Xf) and (XIa) to (XII) and with general formula (XII), (XIII), (XIV), (XV), (XVI) and (XVII) and bonded to an organic or mineral support by a covalent chemical bond and having the following general formulae:

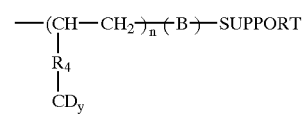 (XVIII)

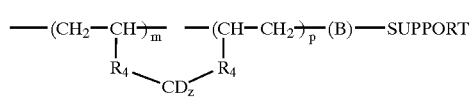 (XIX)

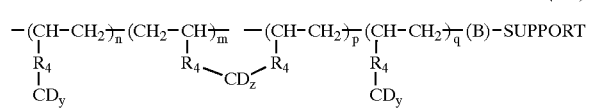 (XX)

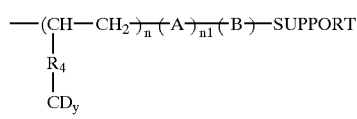 (XXI)

or

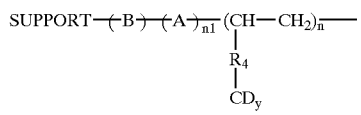

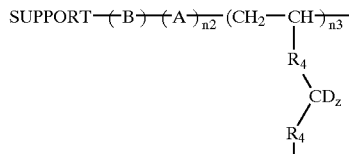

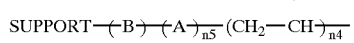

or

 (XXII)

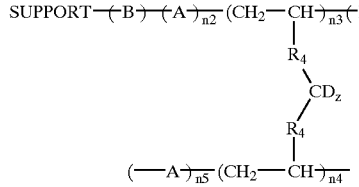

or

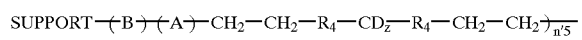 (XXIII)

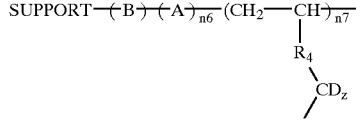

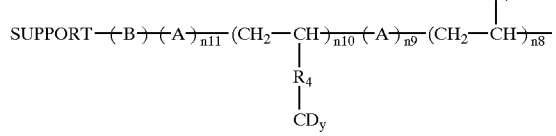

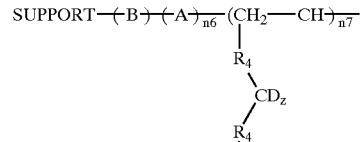

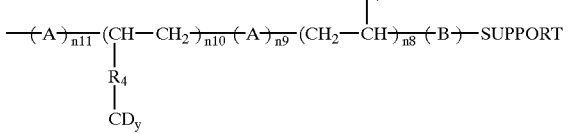

where

"SUPPORT" represents an organic or mineral support functionalised by an alkene or a hydrogenosilane or a sulphydryl;

B represents a single bond, a siloxane or polysiloxane, a silane or polysilane or an ethylene group;

with n, $n_1$, $n_2$, $n_3$, $n_4$, $n_5$, $n'_5$, $n_6$, $n_7$, $n_8$, $n_9$, $n_{10}$, $n_{11}$, m and p, in the range 1 to 100000.

What is claimed is:

1. A composition comprising at least two alkenyl-derivatized cyclodextrins selected from the group consisting of the formulae (XIa), (XIb), (XIc), (XId), (XIe), (XIf) (XIg), (XIh), (XIi), (XIj), (XIk) and (XIl),

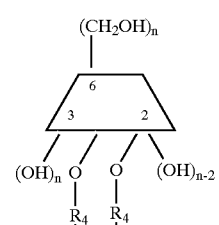 (XIa)

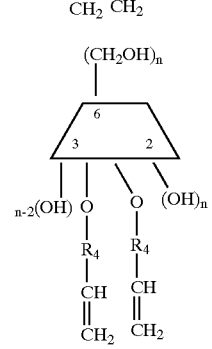 (XIb)

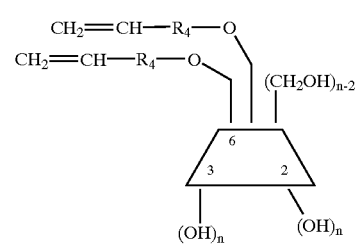 (XIc)

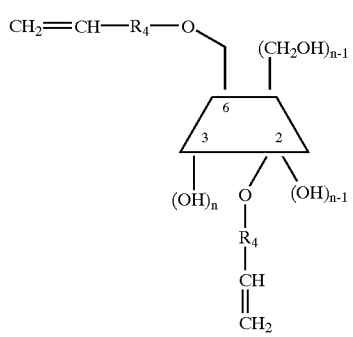
(XId)

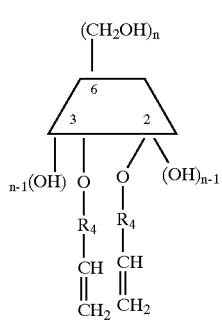
(XIe)

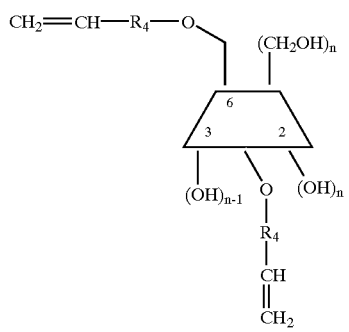
(XIf)

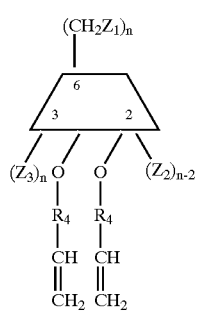
(XIg)

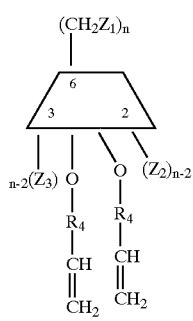
(XIh)

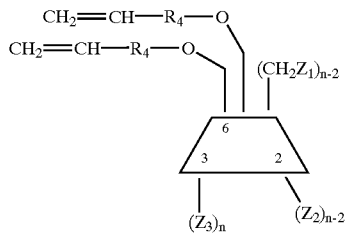
(XIi)

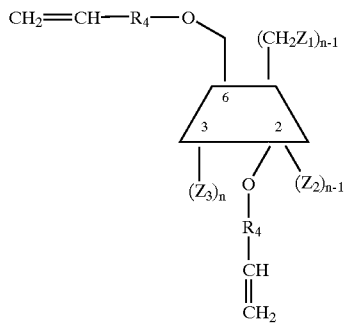
(XIj)

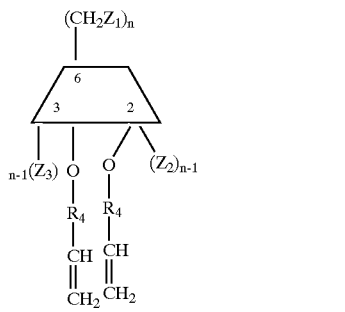
(XIk)

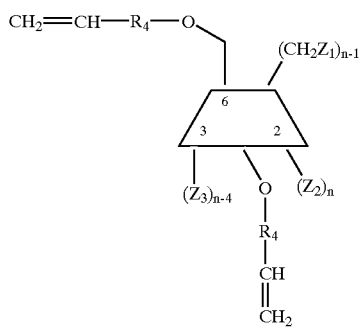
(XIl)

in which
- $R_4$ represents a $C_1$ to $C_{20}$ alkylene group, or an arylene group, optionally substituted by a $C_1$ to $C_{20}$ alkyl group,
- $Z_1$ represents —$Y_1W_1$
- $Z_2$ represents —$Y_2W_2$
- $Z_3$ represents —$Y_3W_3$
- $Y_1$, $Y_2$ and $Y_3$, which maybe identical or different, represent an oxygen atom, a sulphur atom, an amino group, or a sulphoxide or sulphone group;
- $W_1$, $W_2$ and $W_3$, which may be identical or different, represent:
  - a group $A_2$—$A_1$—$A_0$—, where:
    - $A_0$ represents —CO— or —CS—;
    - $A_1$ represents a bond or a secondary amino group;
    - $A_2$ represents a linear or branched alkyl group ($C_1$–$C_{24}$), optionally substituted by an aryl group, or an aryl group itself optionally substituted by a linear or branched ($C_1$–$C_{24}$) alkyl group, where the aryl groups are optionally substituted by one or more identical or different halogen atoms(s), or linear or branched ($C_1$–$C_6$) alkyl groups(s), or hydroxyl groups, or linear or branched ($C_1$–$C_6$) trihalogenoalkyl groups;

a linear or branched ($C_1$–$C_{24}$) alkyl group; or a ($C_3$–$C_8$) cycloalkyl group;

$Z_1$, $Z_2$ or $Z_3$ each represent a carboxylic acid or ester function, a sulphinamide or sulphimide function, a hydroxyl function, a sulphonic acid function, a sodium, potassium or ammonium sulphate function, an ethyl-, propyl- or butylsulphonic function, a phosphoric acid function or a sodium, lithium, potassium or ammonium phosphate function; or $Z_1$ and $Z_3$ together represent a 3,6-anhydro function; or $Z_2$ and $Z_3$ together represent a 2,3-anhydro function; and n is 6, 7 or 8.

2. A homopolymer or copolymer selected from the group consisting of:

(a) a homopolymer of formula (XIII):

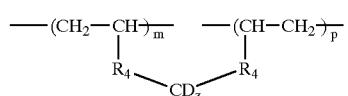

(XIII)

formed by homopolymerization of at least one native or modified cyclodextrin of the formula (XI)

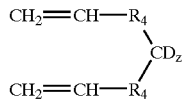

(XI)

where $R_4$ represents a $C_1$ to $C_{20}$ alkylene group or an arylene optionally substituted by a $C_1$ to $C_{20}$ alkyl group, and $CD_z$ represents the divalent residue (II$_z$), (III$_z$), (IV$_z$), (II$_{zz}$), (III$_{zz}$) or (IV$_{zz}$)

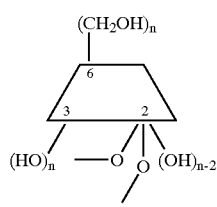

(IIz)

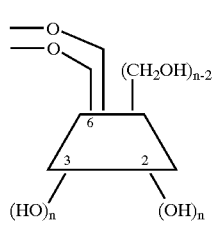

(IIIz)

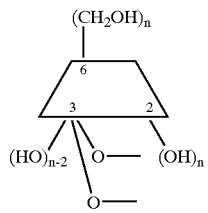

(IVz)

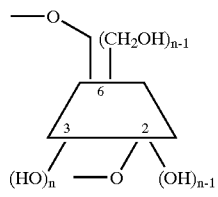

(IIzz)

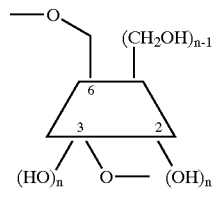

(IIIzz)

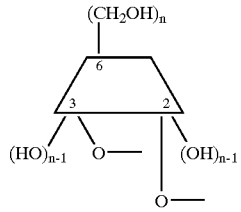

(IVzz)

of said native cyclodextrin or the divalent residue (V$_z$), (VI$_z$), (VII$_z$), (V$_{zz}$), (VI$_{zz}$) or (VII$_{ZZ}$)

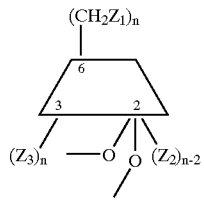

(Vz)

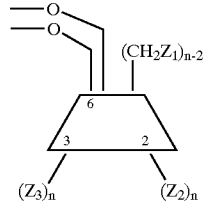

(VIz)

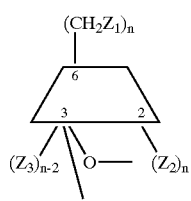

(VIIz)

-continued

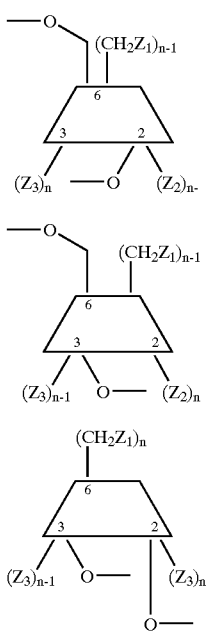

(Vzz)

(VIzz)

(VIIzz)

of said modified cyclodextrin;

and wherein $Z_1$ represents $—Y_1W_1$ $Z_2$ represents $—Y_2W_2$ $Z_3$ represents $—Y_3W_3$ and $Y_1$, $Y_2$ and $Y_3$, which may be identical or different, represent an oxygen atom, a sulphur atom, an amino group, or a sulphoxide or sulphone group;

$W_1$, $W_2$ and $W_3$, which may be identical or different, represent:

a group $A_2—A_1—A_0$:, where:

$A_0$ represents $—CO—$ or $—CS—$;

$A_1$ represents a bond or a secondary amino group;

$A_2$ represents a linear or branched alkyl group ($C_1–C_{24}$), optionally substituted by an aryl group, or an aryl group itself optionally substituted by a linear or branched ($C_1–C_{24}$) alkyl group, the aryl groups also optionally substituted by one or more identical or different halogen atoms(s), or linear or branched ($C_1–C_6$) alkyl group(s), or hydroxyl groups, or linear or branched ($C_1–C_6$) trihalogenoalkyl groups;

a linear or branched ($C_1–C_{24}$) alkyl group; or a ($C_3–C_8$) cycloalkyl group;

$Z_1$, $Z_2$ or $Z_3$ each represents a carboxylic acid or ester function, a sulphinamide or sulphimide function, a hydroxyl function, a sulphonic acid function, a sodium, potassium or ammonium sulphate function, an ethyl-, propyl- or butylsulphonic function, a phosphoric acid function or a sodium, lithium, potassium or ammonium phosphate function; or $Z_1$ and $Z_3$ together represent a 3,6-anhydro function; or $Z_2$ and $Z_3$ together represent a 2,3-anhydro function; and n is 6, 7 or 8;

(b) a homopolymer of formula (XII):

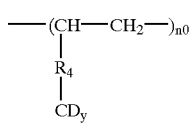

(XII)

formed by homopolymerization of at least one native or modified monosubstituted cyclodextrin of formula (X):

$$CH_2=CH—R_4—CD_y \qquad (X)$$

where $R_4$ represents a $C_1$ to $C_{20}$ alkylene group or an arylene group optionally substituted by a $C_1$ to $C_{20}$ alkyl group, and $CD_y$ represents the monovalent residue ($II_y$), ($III_y$) or ($IV_y$)

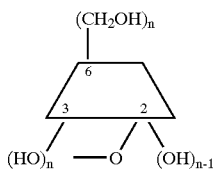

(IIy)

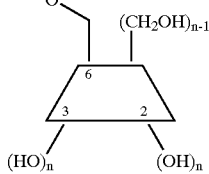

(IIIy)

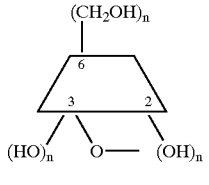

(IVy)

of said native cyclodextrin or the monovalent residue ($V_y$) ($VI_y$) or ($VII_y$);

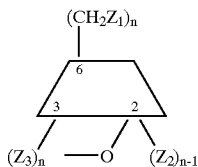

(Vy)

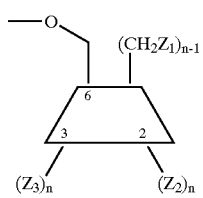

(VIy)

-continued (VIIy)

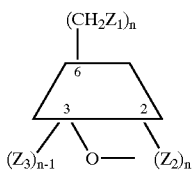

of said modified cyclodextrin, where $Z_1$, $Z_2$, $Z_3$ and n are as defined above;

(c) a copolymer of formula (XIV):

(XIV)

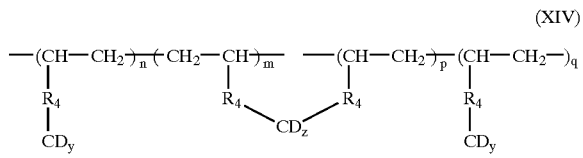

formed by copolymerization of at least one native or modified monosubstituted cyclodextrin of formula (X), defined above, and at least one native or modified disubstituted cyclodextrin of formula (XI), defined above;

(d) a copolymer of formula (XV):

(XV)

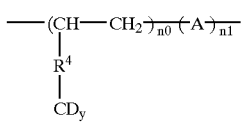

formed by copolymerization of at least one native or modified monosubstituted cyclodextrin of formula (X), defined above, and a bifunctional comonomer A where A is of the formula:

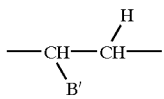

where B' represents an aryl or polyaryl group containing 5 to 30 carbon atoms, or an alkyl group containing 2 to 30 carbon atoms, optionally substituted by a halogen atom; or A is of the formula —X—L—X—
where X represents
  a sulphur atom (thioether function) or a sulphoxide function or a sulphone function;
  L represents $(CH_2)_n$ or an alkylene group, an alkylene substituted by an alcohol or acid function, or an arylene group;

(e) a copolymer of the formulae (XVI):

(XVI)

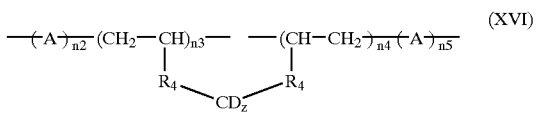

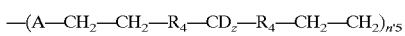

formed by copolymerization of at least one native or modified disubstituted cyclodextrin of formula (XI), defined above, and a bifunctional comonomer A, defined above; and (f) a copolymer of the formula (XVII):

(XVII)

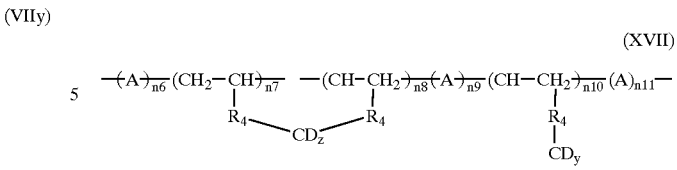

formed by copolymerization of at least one native or modified monosubstituted cyclodextrin of formula (X), defined above, at least one native or modified cyclodextrin of formula (XI), defined above, and a bifunctional comonomer A, defined above;

where for each of (a) through (f), $n_0$ to $n_{10}$, $n'_5$, m and p is from 1 to 10,000.

3. The cyclodextrin of claim 1, wherein at least one of $W_1$, $W_2$, and $W_3$ is methyl, ethyl or hydroxypropyl.

4. A method for synthesizing a monosubstituted derivative of native cyclodextrin of formula (X):

$$CH_2=CH-R_4-CD_y \qquad (X)$$

where $R_4$ represents a $C_1$ to $C_{20}$ alkylene group or an arylene group, optionally substituted by a $C_1$ to $C_{20}$ alkyl group, and $CD_y$ represents the residue $(II_y)$ $(III_y)$ or $(IV_y)$ (IIy)

(IIIy)

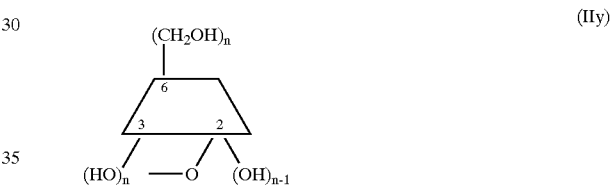

(IVy)

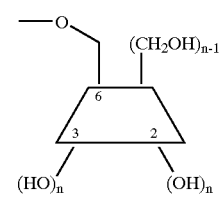

of said native cyclodextrin;

or a disubstituted derivative of native cyclodextrin of formula (XI):

(XI)

where $R_4$ represents a $C_1$ to $C_{20}$ alkylene group, or an arylene group, optionally substituted by a $C_1$ to $C_{20}$ alkyl group, and $CD_z$ represents the divalent residue $(II_z)$, $(III_z)$, $(IV_z)$, $(II_{zz})$, $(III_{zz})$ or $(IV_{zz})$

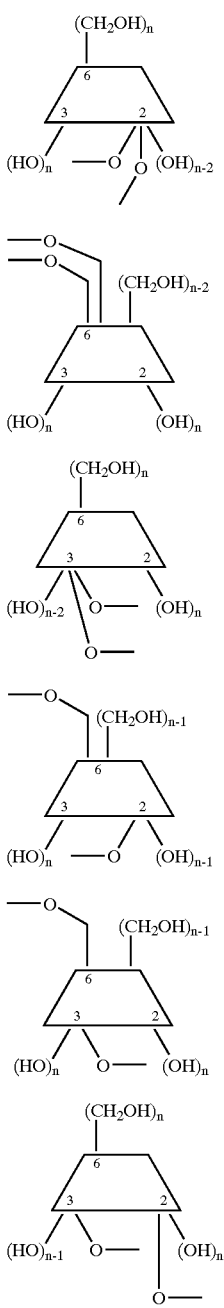

of said native cyclodextrin; comprising reacting a native cyclodextrin with the formula:

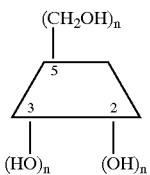

with a compound with formula T—R$_4$—CH=CH$_2$, in which R$_4$ has the same meaning as that given above and T represents a halogen atom, or tosyl or a mesyl radical, said compound T—R$_4$—CH=CH$_2$ being used in a proportion of 1 to 24 moles per mole of a native cyclodextrin.

5. A method for synthesizing a monosubstituted derivative of modified cyclodextrin of formula (X)

$$CH_2=CH-R_4-CD_y \quad (X)$$

where R$_4$ represents a C$_1$ to C$_{20}$ alkylene group or an arylene group, optionally substituted by a C$_1$ to C$_{20}$ alkyl group; CD$_y$ represents the monovalent residue (V$_y$), (VI$_y$) or (VII$_y$) of said modified cyclodextrin;

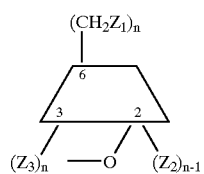

(V$_y$)

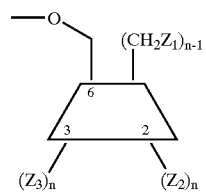

(VI$_y$)

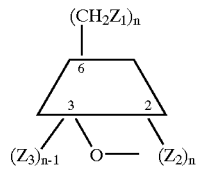

(VII$_y$)

or a disubstituted derivative of modified cyclodextrin of formula (XI):

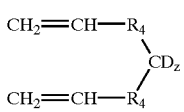

(XI)

where

R$_4$ represents a C$_1$ to C$_{20}$ alkylene group or arylene group, optionally substituted by a C$_1$ to C$_{20}$ alkyl group;

CD$_z$ represents the divalent residue (V$_z$), (VI$_z$), (VII$_z$), (V$_{zz}$), (VI$_{zz}$) or (VII$_{zz}$) of said modified cyclodextrin;

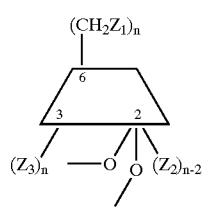

(V$_z$)

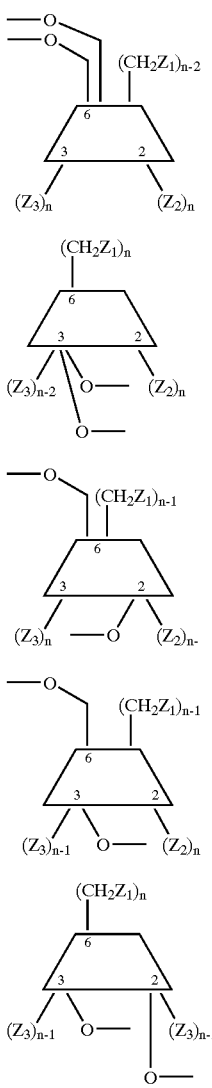

(VIz)

(VIIz)

(Vzz)

(VIzz)

(VIIzz)

and where $Z_1$ represents $—Y_1W_1$ $Z_2$ represents $—Y_2W_2$ $Z_3$ represents $—Y_3W_3$ and $Y_1$, $Y_2$ and $Y_3$, which may be identical or different, represent an oxygen atom, a sulphur atom, an amino group, or a sulphoxide or sulphone group;

$W_1$, $W_2$ and $W_3$, which may be identical or different, represent:

a group $A_2—A_1—A_0—$, where:

$A_0$ represents $—CO—$ or $—CS—$;

$A_1$ represents a bond or a secondary amino group;

$A_2$ represents a linear or branched alkyl group ($C_1$–$C_{24}$), optionally substituted by an aryl group, or an aryl group itself optionally substituted by a linear or branched ($C_1$–$C_{24}$) alkyl group, the aryl groups also optionally substituted by one or more identical or different halogen atoms(s), or linear or branched ($C_1$–$C_6$) alkyl group(s), or hydroxyl groups, or linear or branched ($C_1$–$C_6$) trihalogenoalkyl groups;

a linear or branched ($C_1$–$C_{24}$) alkyl group; or a ($C_3$–$C_8$) cycloalkyl group;

$Z_1$, $Z_2$ or $Z_3$ each represents a carboxylic acid or ester function, a sulphinamide or sulphimide function, a hydroxyl function, a sulphonic acid function, a sodium, potassium or ammonium sulphate function, an ethyl-, propyl- or butylsulphonic function, a phosphoric acid function or a sodium, lithium, potassium or ammonium phosphate function; or $Z_1$ and $Z_3$ together represent a 3,6-anhydro function; or $Z_2$ and $Z_3$ together represent a 2,3-anhydro function; and n is 6, 7 or 8;

comprising reacting a modified cyclodextrin with the formula:

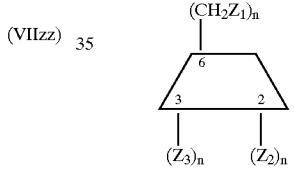

with a compound with formula $T—R_4—CH=CH_2$, in which $R_4$ has the same meaning as that given above and T represents a halogen atom, or a mesyl radical, said compound $T—R_4—CH=CH_2$ being used in a proportion of 1 to 24 moles per mole of modified cyclodextrin.

6. The method of claim 5, wherein at least one of $W_1$, $W_2$, and $W_3$ is methyl, ethyl or hydroxypropyl.

* * * * *